US012633421B2

(12) United States Patent
Johnson et al.

(10) Patent No.: US 12,633,421 B2
(45) Date of Patent: May 19, 2026

(54) SYSTEMS AND METHODS FOR GENERATING DATA RECORDS AND DISPLAYING THE DATA RECORDS ON A GRAPHICAL USER INTERFACE

(71) Applicant: Veeva Systems Inc., Pleasanton, CA (US)

(72) Inventors: Bryan Wayne Johnson, Brookline, MA (US); Myrto M. Miltiadous, New York, NY (US); Christopher George Glazner, New York, NY (US); Vasile Iulian Ilies, Boston, MA (US); Eshaan Ghosh, Milton (CA); Jessica Chau, Richmond Hill (CA); Youzhi Wu, Summit, NJ (US)

(73) Assignee: Veeva Systems Inc., Pleasanton, CA (US)

( * ) Notice: Subject to any disclaimer, the term of this patent is extended or adjusted under 35 U.S.C. 154(b) by 0 days.

(21) Appl. No.: 19/345,911

(22) Filed: Sep. 30, 2025

(65) Prior Publication Data

US 2026/0094728 A1     Apr. 2, 2026

Related U.S. Application Data

(60) Provisional application No. 63/700,947, filed on Sep. 30, 2024.

(51) Int. Cl.
*G16H 50/70*          (2018.01)
(52) U.S. Cl.
CPC ................................. *G16H 50/70* (2018.01)
(58) Field of Classification Search
CPC ........ G16H 50/70; G16H 20/00; G16H 20/10; G16H 20/13; G16H 20/17; G16H 30/20;

(Continued)

(56) References Cited

U.S. PATENT DOCUMENTS 8,595,206 B1    11/2013   Ansari et al.
8,918,385 B1    12/2014   Ansari et al.
(Continued)

FOREIGN PATENT DOCUMENTS

WO      WO-2023150428 A1 *   8/2023   ............. G16H 50/30
WO      WO-2024233438 A1 *  11/2024   ............. G16H 40/63

OTHER PUBLICATIONS

J. Guan, R. Li, S. Yu and X. Zhang, "Generation of Synthetic Electronic Medical Record Text," 2018 IEEE International Conference on Bioinformatics and Biomedicine (BIBM), Madrid, Spain, 2018, pp. 374-380. (Year: 2018).*

(Continued)

*Primary Examiner* — Christopher L Gilligan
*Assistant Examiner* — Tristan Isaac Evans

(57)          ABSTRACT

A method for generating an electronic file including receiving multiple first data records. The method further includes selecting a first digital projection model and a second digital projection model. The method further includes determining a first set of digitally projected records using the first digital projection model and determining a second set of digitally projected records using the second digital projection model. The method further includes receiving a plurality of new first data records. The method further includes determining a third set of digitally projected records using the first digital projection model. The method further includes receiving a file generation request including a file destination address and generating the electronic file including at least one digitally projected record of the third set of digitally projected records. The method further includes providing the electronic file to the file destination address of the file generation request.

20 Claims, 16 Drawing Sheets

(58) Field of Classification Search
CPC ........ G16H 30/40; G16H 40/00; G16H 40/20;
G16H 40/40; G16H 40/60; G16H 40/63;
G16H 40/67; G16H 50/50; G16H 50/20;
G16H 50/30
See application file for complete search history.

(56) References Cited

U.S. PATENT DOCUMENTS

| | | | |
|---|---|---|---|
| 8,928,606 B1 * | 1/2015 | Khafizova | G16H 50/70 |
| | | | 715/702 |
| 10,185,809 B1 | 1/2019 | Zhou et al. | |
| 10,231,077 B2 | 3/2019 | Raduchel et al. | |
| 10,553,307 B2 | 2/2020 | Connely, IV et al. | |
| 10,586,614 B1 | 3/2020 | Cai et al. | |
| 10,755,812 B1 | 8/2020 | Cai et al. | |
| 10,769,181 B2 | 9/2020 | Bari et al. | |
| 10,937,531 B1 | 3/2021 | Wang et al. | |
| 11,107,578 B2 | 8/2021 | Nag | |
| 11,551,794 B1 | 1/2023 | Lofgren et al. | |
| 11,575,673 B2 | 2/2023 | Padmani et al. | |
| 11,783,922 B1 | 10/2023 | Tong et al. | |
| 11,868,506 B2 | 1/2024 | Johnson et al. | |
| 11,948,112 B2 | 4/2024 | Crooks et al. | |
| 11,989,326 B2 | 5/2024 | Levy et al. | |
| 12,019,597 B1 | 6/2024 | George et al. | |
| 12,094,588 B1 | 9/2024 | Hermey et al. | |
| 12,248,526 B1 | 3/2025 | Pushparajah et al. | |
| 12,406,754 B1 | 9/2025 | Evenhaim et al. | |
| 12,424,304 B1 | 9/2025 | Evenhaim et al. | |
| 2002/0111833 A1 | 8/2002 | Dick | |
| 2002/0116227 A1 | 8/2002 | Dick | |
| 2002/0165736 A1 | 11/2002 | Tolle et al. | |
| 2008/0300902 A1 | 12/2008 | Smith et al. | |
| 2008/0306872 A1 | 12/2008 | Felsher | |
| 2009/0048877 A1 | 2/2009 | Binns et al. | |
| 2010/0131284 A1 | 5/2010 | Duffy | |
| 2010/0241595 A1 | 9/2010 | Felsher | |
| 2010/0324936 A1 | 12/2010 | Vishnubhatla et al. | |
| 2011/0112862 A1 | 5/2011 | Yu | |
| 2011/0112970 A1 | 5/2011 | Yu | |
| 2011/0119088 A1 | 5/2011 | Gunn | |
| 2011/0191343 A1 | 8/2011 | Heaton et al. | |
| 2012/0046972 A1 | 2/2012 | Tonti et al. | |
| 2012/0191749 A1 | 7/2012 | New et al. | |
| 2013/0073313 A1 | 3/2013 | Christakis et al. | |
| 2013/0291060 A1 | 10/2013 | Moore | |
| 2014/0129256 A1 | 5/2014 | Veren | |
| 2014/0136237 A1 | 5/2014 | Anderson et al. | |
| 2014/0298030 A1 | 10/2014 | Akiyama et al. | |
| 2015/0046192 A1 | 2/2015 | Raduchel | |
| 2015/0112979 A1 | 4/2015 | Vittorio | |
| 2015/0347599 A1 | 12/2015 | McMains et al. | |
| 2016/0004820 A1 | 1/2016 | Moore | |
| 2016/0147945 A1 | 5/2016 | MacCarthy et al. | |

| | | |
|---|---|---|
| 2016/0210427 A1 | 7/2016 | Mynhier et al. |
| 2016/0358295 A1 | 12/2016 | Heffley et al. |
| 2017/0004266 A1 | 1/2017 | Vanderhoef |
| 2017/0161439 A1 | 6/2017 | Raduchel et al. |
| 2018/0121614 A1 | 5/2018 | Connely, IV et al. |
| 2018/0294048 A1 | 10/2018 | Blumenthal et al. |
| 2018/0322946 A1 | 11/2018 | Ika et al. |
| 2019/0156927 A1 | 5/2019 | Virkar et al. |
| 2019/0252049 A1 | 8/2019 | Fotsch et al. |
| 2019/0304578 A1 | 10/2019 | Kain et al. |
| 2020/0005900 A1 | 1/2020 | Cha et al. |
| 2020/0035341 A1 | 1/2020 | Kain et al. |
| 2020/0050949 A1 | 2/2020 | Sundararaman et al. |
| 2020/0065410 A1 | 2/2020 | Craig et al. |
| 2020/0202040 A1 | 6/2020 | Johnson et al. |
| 2020/0234826 A1 | 7/2020 | Said |
| 2020/0294642 A1 | 9/2020 | Bostic et al. |
| 2021/0019296 A1 | 1/2021 | Petersen et al. |
| 2022/0117692 A1 | 4/2022 | Sellberg et al. |
| 2022/0270129 A1 | 8/2022 | Dakic et al. |
| 2022/0270729 A1 | 8/2022 | Saliman et al. |
| 2022/0319643 A1 | 10/2022 | Skees et al. |
| 2022/0319697 A1 | 10/2022 | Morris et al. |
| 2023/0104655 A1 | 4/2023 | Amarasingham et al. |
| 2023/0110360 A1 | 4/2023 | Sanae et al. |
| 2023/0144503 A1 | 5/2023 | Powers et al. |
| 2023/0148326 A1 | 5/2023 | Papel et al. |
| 2023/0206329 A1 | 6/2023 | Cella et al. |
| 2023/0273848 A1 | 8/2023 | Vera-Ciro et al. |
| 2023/0282322 A1 | 9/2023 | Rajkumar et al. |
| 2023/0368878 A1 | 11/2023 | Molenda |
| 2023/0385450 A1 | 11/2023 | Bessette et al. |
| 2024/0013899 A1 | 1/2024 | Youngblood et al. |
| 2024/0105289 A1 | 3/2024 | Khan et al. |
| 2024/0112767 A1 | 4/2024 | Thomas, III et al. |
| 2024/0112771 A1 | 4/2024 | Shelton, IV et al. |
| 2024/0127932 A1 | 4/2024 | Bongiovanni et al. |
| 2025/0006352 A1 | 1/2025 | Schoenberg |
| 2025/0046065 A1 | 2/2025 | Goel et al. |
| 2025/0132043 A1 | 4/2025 | Ouimet |
| 2025/0166762 A1 | 5/2025 | Barkol et al. |
| 2025/0190621 A1 | 6/2025 | Boominathan et al. |

OTHER PUBLICATIONS

K. Hydock, A. Elliott, M. Busch, L. Lipchak, D. Blair and J. Chapman, "Generation of Synthetic Data for Medical Decision Support Applications," 2023 IEEE Applied Imagery Pattern Recognition Workshop (AIPR), St. Louis, MO, USA, 2023, pp. 1-7. (Year: 2023).*

Buczak, A.L., Babin, S. & Moniz, L. Data-driven approach for creating synthetic electronic medical records. BMC Med Inform Decis Mak 10, 59 (2010). (Year: 2010).*

Goncalves et al. BMC Medical Research Methodology (2020) 20:108 (Year: 2020).*

* cited by examiner

200

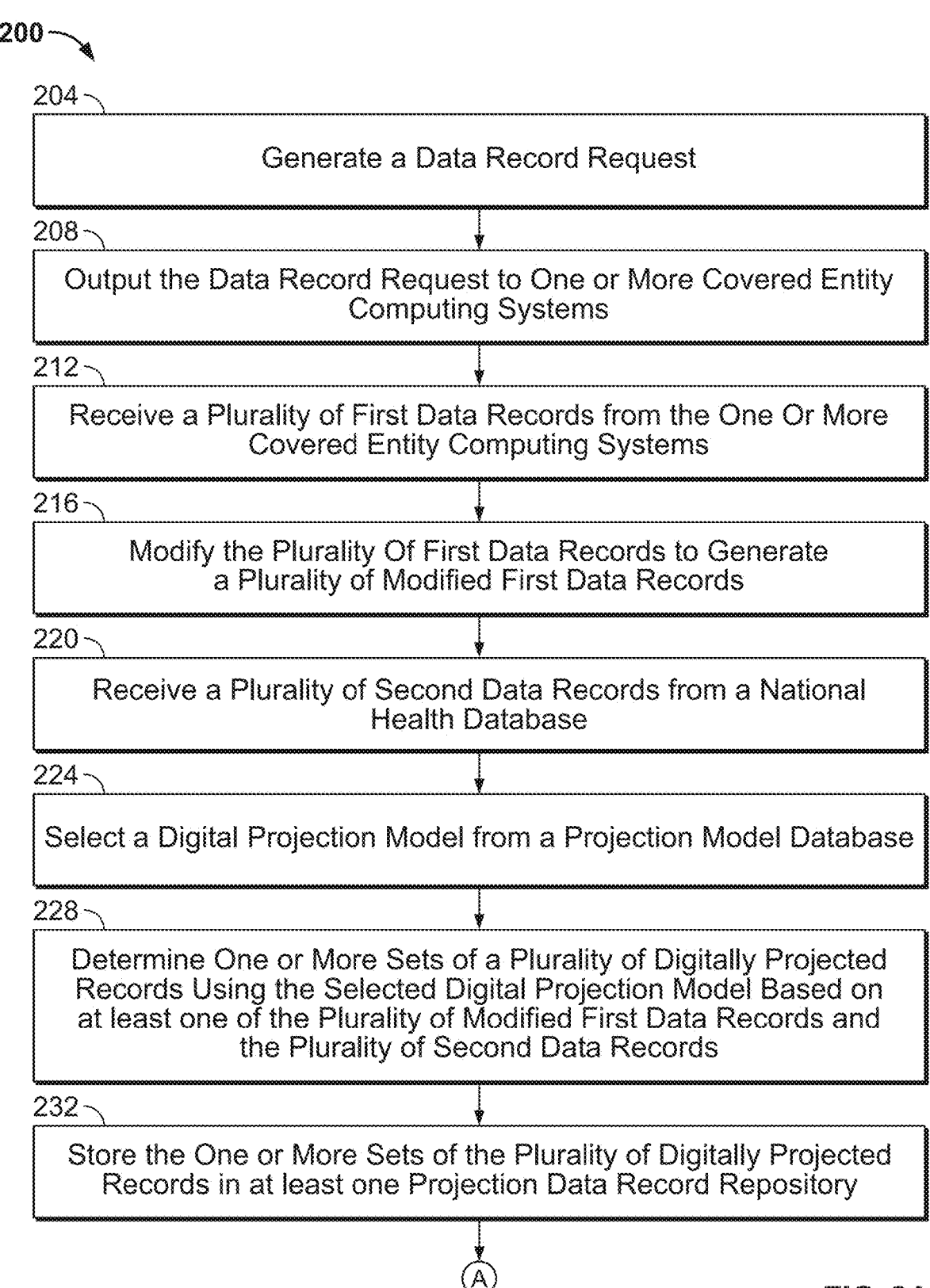

204

Generate a Data Record Request

208

Output the Data Record Request to One or More Covered Entity Computing Systems

212

Receive a Plurality of First Data Records from the One Or More Covered Entity Computing Systems

216

Modify the Plurality Of First Data Records to Generate a Plurality of Modified First Data Records

220

Receive a Plurality of Second Data Records from a National Health Database

224

Select a Digital Projection Model from a Projection Model Database

228

Determine One or More Sets of a Plurality of Digitally Projected Records Using the Selected Digital Projection Model Based on at least one of the Plurality of Modified First Data Records and the Plurality of Second Data Records

232

Store the One or More Sets of the Plurality of Digitally Projected Records in at least one Projection Data Record Repository

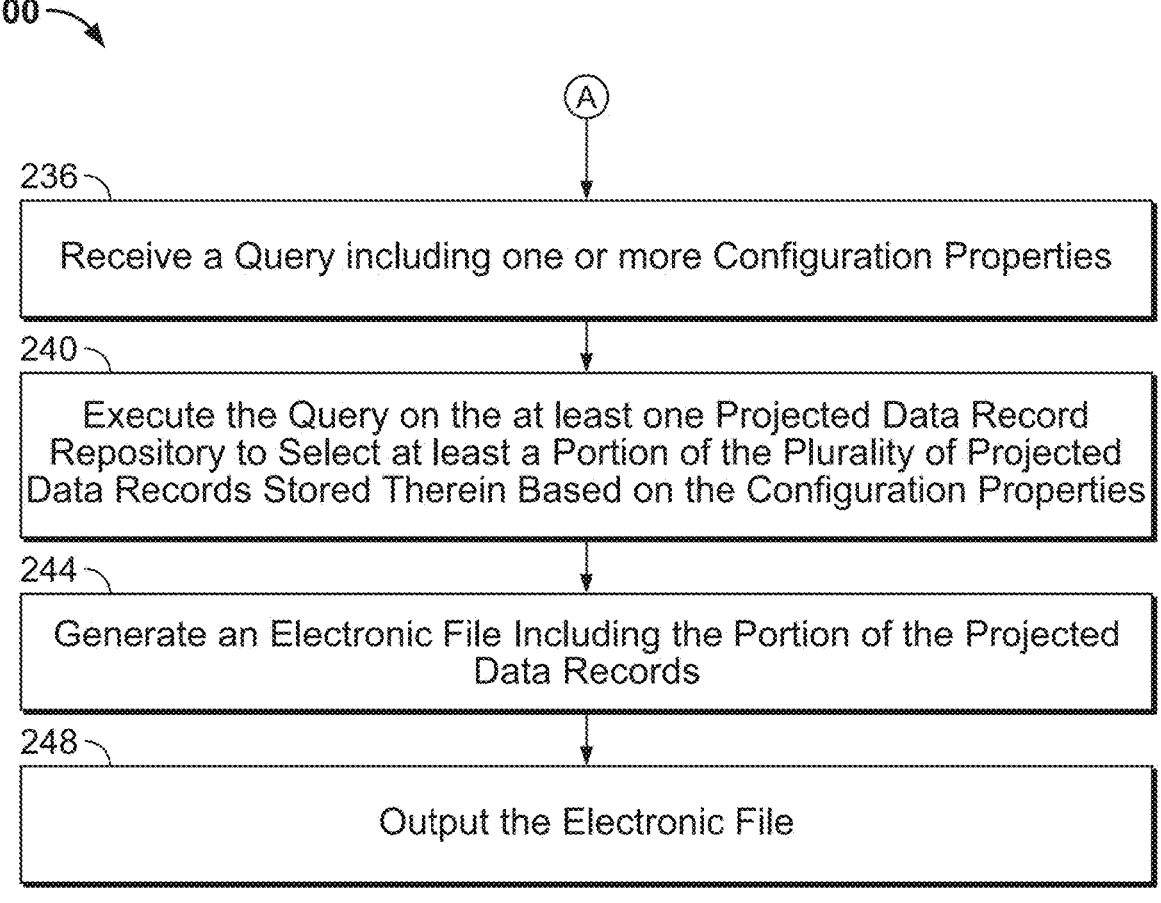

200

Ⓐ

236
Receive a Query including one or more Configuration Properties

240
Execute the Query on the at least one Projected Data Record Repository to Select at least a Portion of the Plurality of Projected Data Records Stored Therein Based on the Configuration Properties 244
Generate an Electronic File Including the Portion of the Projected Data Records 248
Output the Electronic File

FIG. 2B

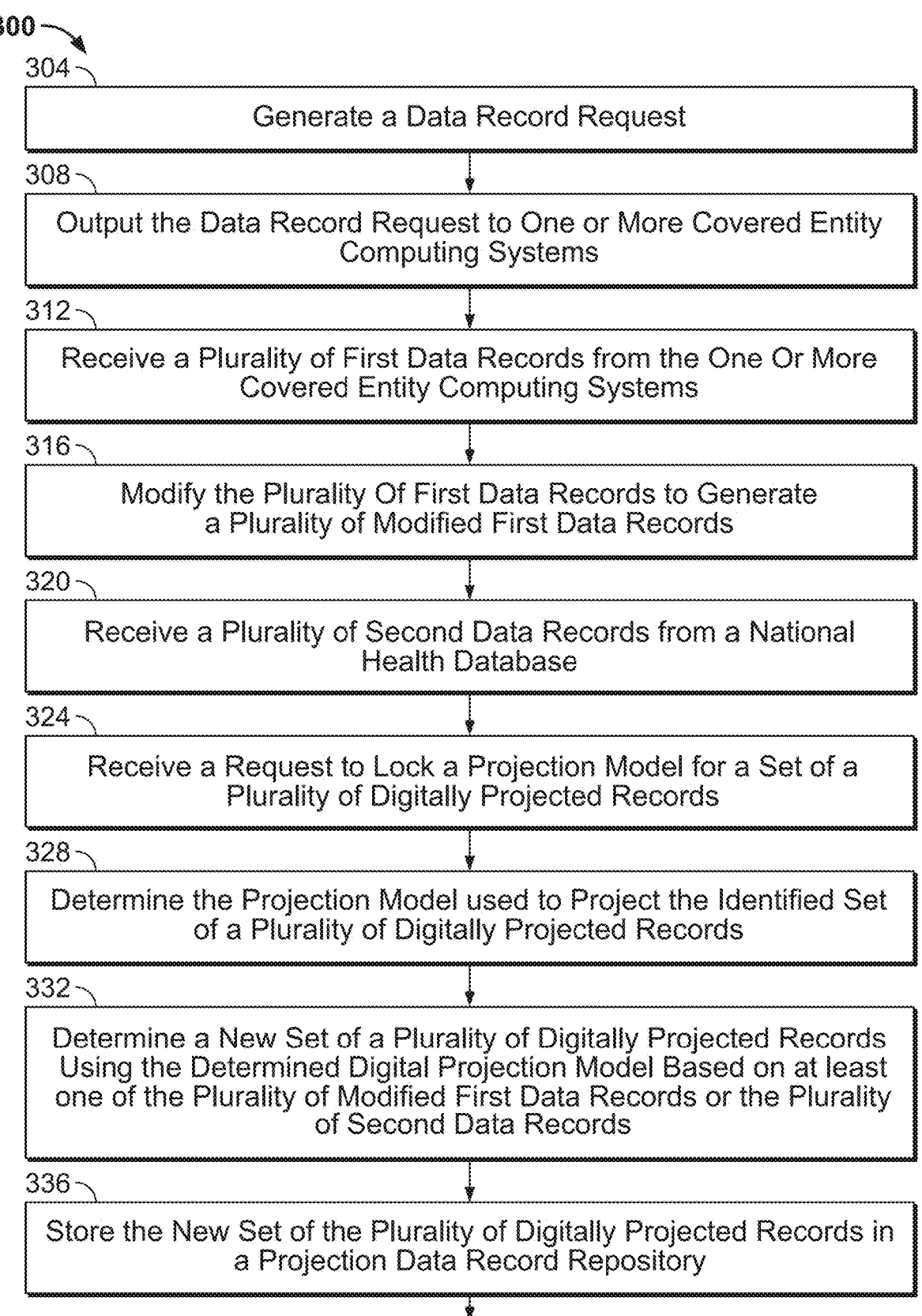

300

304
Generate a Data Record Request

308
Output the Data Record Request to One or More Covered Entity Computing Systems 312
Receive a Plurality of First Data Records from the One Or More Covered Entity Computing Systems 316
Modify the Plurality Of First Data Records to Generate a Plurality of Modified First Data Records 320
Receive a Plurality of Second Data Records from a National Health Database 324
Receive a Request to Lock a Projection Model for a Set of a Plurality of Digitally Projected Records 328
Determine the Projection Model used to Project the Identified Set of a Plurality of Digitally Projected Records 332
Determine a New Set of a Plurality of Digitally Projected Records Using the Determined Digital Projection Model Based on at least one of the Plurality of Modified First Data Records or the Plurality of Second Data Records 336
Store the New Set of the Plurality of Digitally Projected Records in a Projection Data Record Repository

SYSTEMS AND METHODS FOR GENERATING DATA RECORDS AND DISPLAYING THE DATA RECORDS ON A GRAPHICAL USER INTERFACE

CROSS-REFERENCE TO RELATED APPLICATIONS

This application claims priority to U.S. Provisional Patent Application No. 63/700,947, filed Sep. 30, 2024, which is hereby incorporated by reference in its entirety.

TECHNICAL FIELD

The present disclosure relates to systems and methods for generating data records and displaying the data records on a graphical user interface.

BACKGROUND

Researchers, scientists, industry players, academics, government regulators, and other stakeholders are increasingly in need of ways to generate projected data records that are stable over time.

SUMMARY

One embodiment relates to a method for generating an electronic file. The method includes receiving multiple first data records from a covered entity computing system. The method further includes modifying the plurality of first data records to generate a plurality of modified first data records. The method further includes receiving a plurality of second data records from a national health repository and selecting a first digital projection model and a second digital projection model. The method further includes determining a first set of digitally projected records using the first digital projection model based on at least one of: the plurality of modified first data records or the plurality of second data records. The method further includes determining a second set of digitally projected records using the second digital projection model based on at least one of: the plurality of modified first data records or the plurality of second data records. The method further includes selecting the first set of digitally projected records as a final set of digitally projected records and storing the selected first set of digitally projected records in a repository. The method further includes receiving a request to lock the first digital projection model. The method further includes receiving a plurality of new first data records from the covered entity computing system and modifying the plurality of new first data records to generate a plurality of modified new first data records. The method further includes receiving a plurality of new second data records from a national health repository. The method further includes determining a third set of digitally projected records using the first digital projection model based on at least one of: the plurality of modified new first data records or the plurality of new second data records and storing the third set of digitally projected records in the repository. The method further includes receiving a file generation request including a file destination address and generating the electronic file including at least one digitally projected record of the third set of digitally projected records. The method further includes providing the electronic file to the file destination address of the file generation request.

Another embodiment relates to a method for generating an electronic file. The method includes receiving multiple first data records from a covered entity computing system. The method further includes modifying the plurality of first data records to generate a plurality of modified first data records. The method further includes selecting a first digital projection model and a second digital projection model. The method further includes training the first digital projection model to generate a plurality of first model parameters. The method further includes determining a first set of digitally projected records using the first digital projection model based on he plurality of modified first data records and the plurality of first model parameters. The method further includes training the second digital projection model to generate a plurality of second model parameters. The method further includes determining a second set of digitally projected records using the second digital projection model based on the plurality of modified first data records and the plurality of second model parameters. The method further includes selecting the first set of digitally projected records as a final set of digitally projected records and storing the selected first set of digitally projected records in a first repository. The method further includes storing the plurality of first model parameters in a second repository. The method further includes receiving a plurality of new first data records from the covered entity computing system and modifying the plurality of new first data records to generate a plurality of modified new first data records. The method further includes selecting the plurality of first model parameters from the second repository. The method further includes determining a third set of digitally projected records using the first digital projection model based on the plurality of modified new first data records and the plurality of first model parameters and storing the third set of digitally projected records in the repository. The method further includes receiving a file generation request including a file destination address and generating the electronic file including at least one digitally projected record of the third set of digitally projected records. The method further includes providing the electronic file to the file destination address of the file generation request.

Another embodiment relates to a method for generating an electronic file. The method includes receiving multiple first data records from a covered entity computing system. The method further includes modifying the plurality of first data records to generate a plurality of modified first data records. The method further includes selecting a first digital projection model and a second digital projection model. The method further includes determining a first set of digitally projected records using the first digital projection model based on the plurality of modified first data records. The method further includes determining a second set of digitally projected records using the second digital projection model based on the plurality of modified first data records. The method further includes selecting the first set of digitally projected records as a final set of digitally projected records and storing the selected first set of digitally projected records in a repository. The method further includes receiving a request to lock the first digital projection model. The method further includes receiving a plurality of new first data records from the covered entity computing system and modifying the plurality of new first data records to generate a plurality of modified new first data records. The method further includes determining a third set of digitally projected records using the first digital projection model based on at least one of: the plurality of modified new first data records or the plurality of first data records and storing the third set of digitally projected records in the repository. The method further includes receiving a file generation request including a file destination address and a query. The query includes a configuration property. The method further includes executing the query on the repository to select at least one digitally projected record of the third set of digitally projected records based on the configuration property. The method further includes generating the electronic file including the at least one digitally projected record of the third set of digitally projected records. The method further includes providing the electronic file to the file destination address of the file generation request.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE FIGURES

FIGS. 2A-2B are a flow diagram of a method for generating a first set of projected data records and querying the first set of projected data records from a repository, according to an example embodiment.

FIGS. 3A-3B are a flow diagram of a method for generating a new set of projected data records and querying the new set of projected data records from a repository, according to an example embodiment.

DETAILED DESCRIPTION

Figure 1:
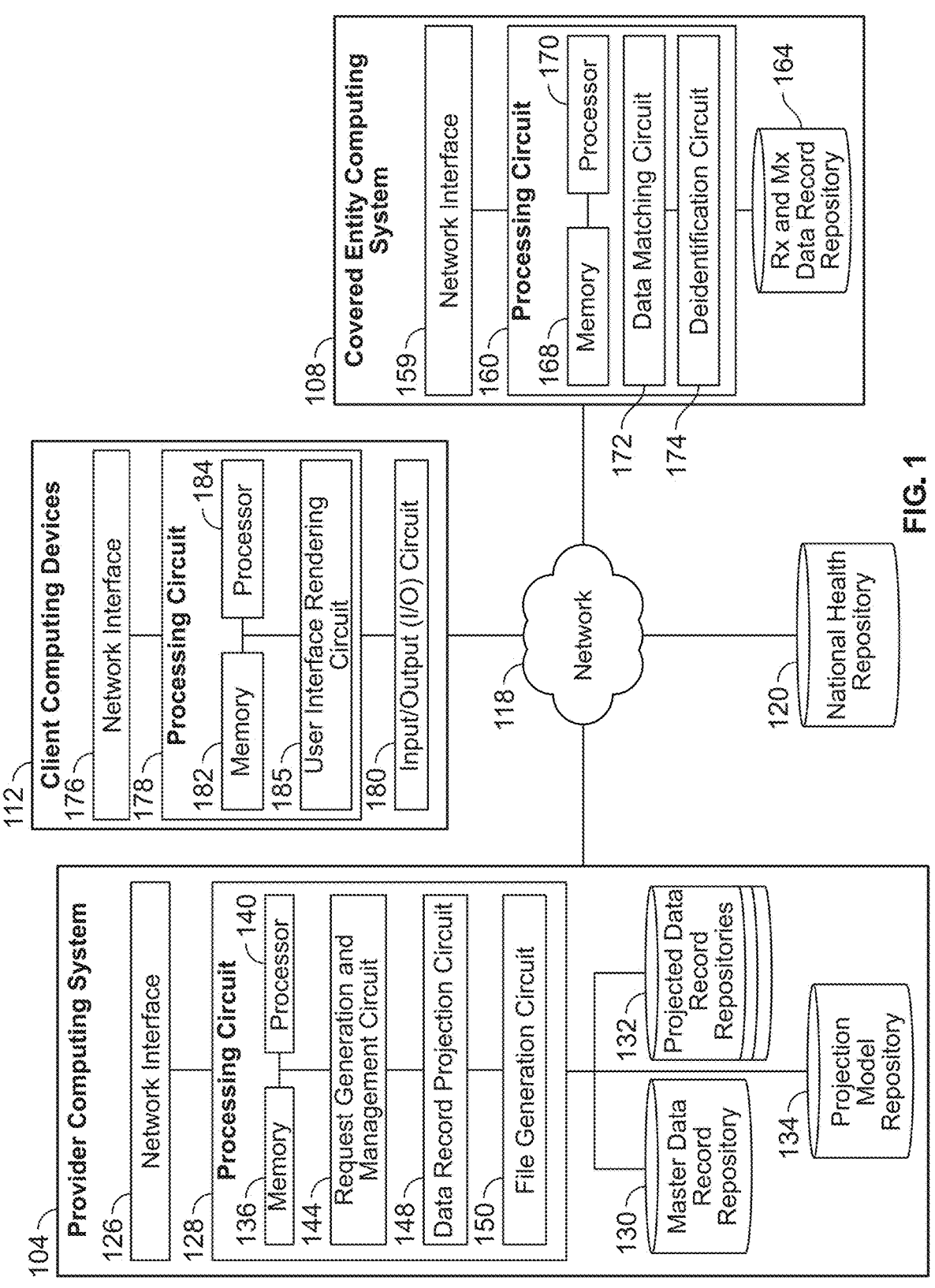
FIG. 1 is a component diagram of a query generation and health data analyzation system, according to an example embodiment.

Referring generally to the figures, systems and methods for generating data records and displaying the data records on a Graphical User Interface (GUI) are disclosed. The systems and methods described herein provide a technical improvement to computer graphing systems and methods for graphing prescriber values. For instance, because the present systems and methods group projected data records into a lesser number of bins or buckets and then assign each bin or bucket the lowest values of the data, the present systems and methods provide for reduced computation complexity. For instance, by working with buckets instead of individual data points, the present systems and method significantly reduce the computational cost and required processing power for visualizing the large datasets because the present systems and methods operate on the counts or values within assigned to each bucket, performing fewer calculations compared when compared to handling every single data point. This results in faster processing times and improved performance for the interactive or animated chart.

Moreover, by generating a first or original set of data records through a model selection process, and then locking the model thereafter, the present systems and methods provide for more stable and readily-usable sets of projected data records and a technical improvement to data projection methodologies. For instance, because the systems and methods use multiple projection models to project the data records, the present systems provide for improved data accuracy and reduced bias. For example, combining multiple models can reduce the impact of individual model errors, leading to more accurate predictions. Likewise, by choosing the best performing model, the present systems and methods can significantly improve the accuracy of the projected data records and reduce bias that might be inherent in any single model. However, once the model is selected and locked, it provides a stable foundation for future projections, reducing the risk of sudden and unpredictable changes. In comparison, typical data projection systems may attempt to create more stable projected data by considering the previously projected value as a true value. This can create inherent bias and inaccuracy in the model, which only grows as future projections are made based on that value, the following value, and so on. In comparison, the present systems and methods only treat actual values as true (e.g., the first data records and the second data records), then select the highest-rated projection model that fits the actual data. Then, the present systems and methods enact a method-lock utilizing that same projection model to generate future predictions, which creates stability in the projections and ensures that projections are comparable over time.

Likewise, because the electronic file described herein is dynamically generated as a specified file type, as decided by the user or the computing device/system to which the electronic file is provided, the systems and methods described herein may provide for improved shareability of the electronic file as well as use less processing power and memory. For example, in situations where the electronic file is only generated as a static file type, third-party computing systems and recipient computing devices (e.g., the recipient computing device) may have to perform additional file modification and conversion or request the provider computing system to do so, which requires additional processing power, memory (to keep two files), and time. In comparison, the systems and methods described herein allow the user to specify the file type of the electronic file through the electronic file generation request. Accordingly, the user can specify the wanted file type the first time and the provider computing system will generate the electronic file as the specified file type. As a result, no additional file modification or conversion is required, reducing processing power usage, memory usage, and overall processing time for the provider computing system.

By utilizing and verifying the digital projection model data schema or model format, the present systems and methods provide a technical improvement to model performance, reliability, and maintainability, as well as enhanced model robustness and stability. For instance, because the digital projection models are trained on a specific data format, including data types, column names, and value ranges, the specific format of the data schema provides for data integrity. For instance, if the data schema or model is new, unseen data changes, degrade the model's performance or it might fail entirely. For example, a model expecting a numerical feature might fail if it receives a categorical one instead. By using data schema versions and verifying the schema of incoming data against the expected version, the present systems provide for improved model stability and runtime performance, thereby requiring less processing power and memory by ensuring the model is utilizing the correct data.

Likewise, because the present systems and methods utilizes multiple digital projection models, the model data schema or model format provides for enhanced order and verification. For instance, by verifying the digital projection model based on the model data schema, the present systems and methods ensures that every new batch of data is checked before it's used, which provides for less data incompatibility issues and less errors when running the digital projection model.

As used herein, "data records" "health data records" or "government data records" can include data related to a patient's medical history such as symptoms, diagnosis data (e.g., an ICD-10 diagnosis code), procedures, medical claims (Mx) data, clinical data, electronic health record (EHR) data (including Rx data, lab tests/vitals, and the like), test results, genomic result or genomic test result, prescription claims (Rx) data associated with one or more medical products (e.g., including transaction data, prescribing HCP national prescriber identifier (NPI), medical product data, date/time data, diagnosis data, and the like), medical claims (Mx) data associated with national health insurance (e.g., Medicare or Medicaid) claims data associated with one or more medical products (e.g., including transaction data, prescribing HCP national prescriber identifier (NPI), and medical outcomes. Further, "data records" or "health data records" or "government data records" can include private health data (PHI) or personally identifiable information (PII) such as a patient's name, address, IP address, contact data, and the like.

Additionally, as used herein the terms "information" and "data" may be used interchangeably such that one may be substituted for the other and vice versa.

Referring now to FIG. 1, a system 100 for generating and querying projected data records, according to an example embodiment. The system 100 includes a provider computing system 104, a covered entity computing system 108, a client computing device 112, and a national health repository 120 connected by a secure network (e.g., a network 118).

The network 118 communicably and operably couples the provider computing system 104, the covered entity computing system 108, the client computing device 112, and the national health repository 120 such that communicable and operable computing may be provided between the provider computing system 104, the covered entity computing system 108, the client computing device 112, and the national health repository 120 over the network 118. In various embodiments, the network 118 includes any combination of a local area network (LAN), an intranet, the Internet, or any other suitable communications network, directly or through another interface.

The provider computing system 104 may be operated and managed by a provider (e.g., a software as a service (SaaS) provider, a cloud services provider, a software provider, a service provider, etc.) and may include a computer system (e.g., one or more servers (e.g., a cloud computing server) each with one or more processing circuits). In some embodiments, the provider computing system 104 may act as a host and provide an application (e.g., a web-based application, a mobile application, etc.) to the client computing device 112 over the network 118 in response to authenticating the client computing device 112. In some examples, the provider computing system 104 may be a multi-tenant system where various elements of hardware and software may be shared by one or more customers. In a multi-tenant system, a user is typically associated with a particular customer. In one example, a user (e.g., of the client computing device 112) could be an employee of one of a number of (pharmaceutical) companies which are tenants, or customers, of the provider computing system 104.

In some embodiments, the provider computing system 104 may run on a cloud computing platform. Users can access content on the cloud independently by using a virtual machine image or purchasing access to a service maintained by a cloud repository provider.

In some embodiments, the provider computing system 104 may be provided as Software as a Service ("SaaS") to allow users to access the provider computing system 104 with a thin client.

As shown, the provider computing system 104 may include a network interface 126, a processing circuit 128, and a master data record repository 130, multiple projected data record repositories 132, and a projection model repository 134. In some embodiments, the provider computing system 104 may include an input/output circuit (e.g., similar to (e.g., the same as) an input/output circuit 180 as will described further herein).

The network interface 126 is structured to establish connections with the covered entity computing system 108, the client computing device 112, and the national health repository 120 by way of the network 118. The network interface 126 includes program logic and/or hardware-based components that connect the provider computing system 104 to the network 118. For example, the network interface 126 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 126 includes the hardware and machine-readable media structured to support communication over multiple channels of data communication (e.g., wireless, Bluetooth, near-field communication (NFC). In some embodiments, the network interface 126 includes cryptography logic and capabilities to establish a secure communications session.

The processing circuit 128, as shown, comprises a memory 136, a processor 140, a request generation and management circuit 144, a data record projection circuit 148, and a file generation circuit 150. The memory 136 includes one or more memory devices (e.g., RAM, NVRAM, ROM, flash memory, hard disk storage, etc.) that store data and/or computer code for facilitating the various processes described herein. That is, in operation and use, the memory 136 stores at least portions of instructions and data for execution by the processor 140 to control the processing circuit 128. The memory 136 may be or include tangible, non-transient volatile memory and/or non-volatile memory. The processor 140 may be implemented as a general-purpose processor, an application specific integrated circuit (ASIC), one or more field programmable gate array (FPGAs), a digital signal processor (DSP), a group of processing components or other suitable electronic processing components. As described herein, each circuit of the processing circuit 128 may be associated with a separate server computing system (including a memory and processor therein). For instance, a first server computing device of the provider computing system 104 may perform the operations of the request generation and management circuit 144; a second server computing device of the provider computing system 104 may perform the operations of the data record projection circuit 148; and a third server computing device of the provider computing system 104 may perform the operations of the file generation circuit 150.

As described herein, the request generation and management circuit 144 is configured and/or structured to generate and manage data record requests that may be provided to the covered entity computing system 108. For instance, the request generation and management circuit 144 may be configured or structured to retrieve data included in the data record request (e.g., a timeframe for which data records are sought), Health Care Provider (HCP) data (e.g., from an HCP repository (not shown)) for which matching or associated data records are sought, government health records from the national health repository 120, etc.) for which matching or associated data records are sought, medical product data for which matching or associated data records are sought (e.g., from a medical domain repository (not shown)), or any combination thereof. Further, the request generation and management circuit 144 may be configured or structured to generate the data record request including the data included in the request and provide the data record request to the covered entity computing system 108. In some embodiments, the request generation and management circuit 144 may be configured to generate and provide the data record request to the covered entity computing system 108 at specific time intervals (e.g., every hour, every day, every week, every month, etc.), and, as a result, the provider computing system 104 may receive the data records at the specific time intervals. By doing so, the provider computing system 104 may act as a centralized source of reliable, up to date, data records (e.g., health data records). For instance, because the request generation circuit 144 may generate and provide the data record request to the covered entity computing system 108 at specific time intervals, the provider computing system 104 may receive updated data records at the specific time intervals and continuously keep up-to-date data records.

In some embodiments, the request generation and management circuit 144 is further configured and/or structured to receive a file generation request. The file generation request may identify one or more statistical values and a recipient address (e.g., an IP address, an email address, an FTP address, etc.). In other embodiments, the one or more statistical values and the recipient address may be received within or accompanying a query.

In some embodiments, the request generation and management circuit 144 is further configured and/or structured to receive the requested data records from the covered entity computing system(s) 108, clean and modify the data records, and store the cleaned data records in the master data record repository 130. In other embodiments, other circuits of the processing circuit 128 are configured or structured to receive the requested data records from the covered entity computing system(s) 108 and store the data records in the master data record repository 130.

In some embodiments, the request generation and management circuit 144 is further configured and/or structured to clean the received data records and determine and generate multiple attributes of the data records to augment or add to the data records. For instance, the request generation and management circuit 144 may clean the data records by deduplicating data records that appear multiple times (e.g., removing or combining multiple duplicate records into a single data record). In other examples, the request generation and management circuit 144 may determine and/or generate a reject code classification associated with at least one of the data records and add the reject code classification to the at least one data record. In other embodiments, a data record and attribute management circuit (not shown) of the processing circuit 128 may clean, group, and add attributes to the data records.

The data record projection circuit 148 is configured and/or structured to select one or more digital projection models from the projection model repository 134 and determine one or more sets of projected data records (also referred to as sets of digitally projected values because each projected data record may include a digitally projected record) based on the received government data records, received HCP data, and/or received first data records. For instance, the data record projection circuit 148 may receive or query first data records from the one or more national health repositories 120, receive second data records from the covered entity computing systems 108, and receive or query HCP data from an HCP repository (not shown). Next, the data record projection circuit 148 may select a first digital projection model from the projection model repository 134 and determine a first set of projected data records based on the first data records. Then, the data record projection circuit 148 may determine a second set of projected data records based on the first data records, the second data records, and the HCP data. In some embodiments, a separate modeling circuit (e.g., not shown) may select the one or more digital projection models and determine the one or more sets of projected data records.

Still referring to FIG. 1, the file generation circuit 150 may be configured to receive a query (also referred to as a customizable or mutable query) from the client computing device 112 and execute the query on one of the projected data record repositories 134 to select one or more of the projected data records stored therein. For example, the provider computing system 104 may receive a query that includes multiple configuration properties (also referred to as query parameters) (e.g., a first configuration property and a second configuration property) from the client computing device 112. The first configuration property may identify a specific medical product (e.g., Drug X), and the second configuration property may identify a specific date range (e.g., Jan. 1, 2021-Jan. 1, 2022). In response, the file generation circuit 150 may execute the query on the projected data record repository 134 by selecting or receiving data records that are associated with the medical product (e.g., a prescription for Vaccine Y, EHR indicating a patient received Drug X, etc.) and between the specific date range from the projected data record repository 134.

As described herein, each configuration property may be a property or query parameter through which the provider computing system 104 selects, filters, and refines the projected data records of the projected data record repositories 134. For instance, a first configuration property may identify or include a medical product (e.g., Drug x) for which projected data records are sought. In another example, a second configuration property may identify or include an HCP NPI. Other configuration properties will be described further, but may include procedures (e.g., procedure codes), generated or determine attributes (e.g., transaction status or state (e.g., rejected, dispensed, reversed), rejection code classification, a disposition or order of the data record (e.g., interim record, final record, etc.), etc.), timeframes, demographic features (e.g., gender, age range or age, etc.), location (e.g., zip code, state, country, county, etc.), HCP identifiers (e.g., NPI, specialty, location, medical group, etc.), payment type (e.g., private insurance, national health insurance (e.g., Medicare, Medicaid, Medicare part A-D, etc.)), activity or number of occurrences (e.g., a minimum of 5 prescriptions, a prescription at least once a year, a prescription at least once a quarter, maximum of 10 prescriptions, etc.), prescribing HCP specialty (e.g., Pediatrician, Cardiologist, etc.), and/or a sequence of one or more configuration properties (e.g., a diagnosis of diagnosis code 123 before (i.e., at an earlier date) than a prescription of Drug X, a prescription of Drug X before a procedure for procedure code 123, etc.).

The file generation circuit 150 is further configured and/or structured to generate an electronic file based on the file generation request or the query. For instance, once the file generation circuit 150 has executed the query and selected the matching projected data records, the file generation circuit 150 may generate a file of a specified format (e.g., comma-separated value (CSV) format, Excel (XLS) format, etc.) and populate it with the matching data records. Because the electronic file is generated as a specified file format, the electronic file can be shared with a variety of destinations and quickly parsed and analyzed. In some embodiments, a file generation request may indicate the specified file format that the electronic file is to be.

The master data record repository 130 is a repository (e.g., a database, cloud storage, etc.) that is structured or configured to receive, store, and manage data records (e.g., health data records) received from the one or more covered entity computing systems 108. For example, the master data record repository 130 may receive Rx data, Mx data, EHR, and the like from the one or more covered entity computing systems 108. Each health data record may be associated with a specific medical product(s) (e.g., drug name, one or more substances included in the medical product, trade name, use cases, diagnosis code(s)), deidentified PHI or PII (e.g., tokenized PHI or PII), demographic data (e.g., age range, payer type, zip code, 3-digit zip code, etc.), and/or an HCP (e.g., NPI of the HCP). In some embodiments, the data records may be aggregated by a specific aggregation or granularity type (e.g., patient, HCP, location, etc.). The master data record repository 130 may be considered a trusted or reliable source of data records. Further, the master data record repository 130 can be structured according to various database types, such as, relational, hierarchical, network, flat, point-in time, and/or object relational. In some embodiments, the master data record repository 130 includes a plurality of nonvolatile/non-transitory storage media such as solid-state storage media, hard disk storage media, virtual storage media, cloud-based storage drives, storage servers, and/or the like. In some embodiments, the provider computing system 104 may include a separate repository for each type of health data records (e.g., a prescription claims repository (not shown) for Rx data, a medical claims repository (not shown) for Mx data, an electronic health record repository (not shown) for EHR, etc.).

Likewise, the projected data record repositories 132 may each be a repository for storing the sets of projected data records. In some embodiments, the provider computing system 104 may include a separate projected data record repository 132 for each set of projected data records. In other embodiments, the provider computing system 104 may include a separate projected data record repository 132 for each granularity type (e.g., HCP, location, etc.). Each separate projected data record repository 132 can be structured according to various database types, such as, relational, hierarchical, network, flat, point-in time, and/or object relational. In some embodiments, each separate projected data record repository 132 includes a plurality of nonvolatile/non-transitory storage media such as solid-state storage media, hard disk storage media, virtual storage media, cloud-based storage drives, storage servers, and/or the like.

Similarly, the projection model repository 134 may be a repository (e.g., database) that receives, stores, and manages various digital projection models (e.g., machine-learning (ML) models, statistical models, etc.) used to determine digitally projected data records. To do so, the projection model repository 134 can be structured according to various database types, such as, relational, hierarchical, network, flat, point-in time, and/or object relational. In operation, the projection model repository 134 is configured to store, manage, and provide digital projections models such as ML projection (i.e., forecasting) models (e.g., binary classification models, neural network models (e.g., Convolutional Neural Network (CNN) model, Long Short-Term Memory Networks (LSTMs) models) multiclass classification models, regression models (e.g., linear regression models), etc.).

In some embodiments, the provider computing system 104 further includes a medical domain repository (not shown) that receives, stores, and manages various medical domain data (e.g., medical product data, procedure data (e.g., procedure codes and descriptions), and diagnosis data (e.g., diagnosis codes and descriptions)). While not shown, the medical domain repository may be structured similar to the master data record repository 130. In one instance, the medical domain repository may receive a grouping of multiple drugs or medical products as specified by the user of the client computing device 112. As will be described herein, the grouping of drugs may be utilized by the user in generating the query.

Still referring to FIG. 1, the one or more covered entity computing systems 108 may each include a computer system (e.g., one or more servers each with one or more processing circuits) and be operated by, be managed by, and/or operate on a data network of a "covered entity" as defined by the Health Insurance Portability and Accountability Act of 1996 (HIPAA) (or other laws that protect health data). For example, the covered entity may be a pharmacy chain (e.g., a pharmacy company) with access to prescription claims data, a medical claims company (e.g., a medical insurance company) with access to medical claims data, a medical provider with access to EHR data, or a government entity with access to national health insurance (e.g., Medicare or Medicaid) claims data, and the like. In this regard, the covered entity computing system 108 may have direct access to health data records including PII, PHI, prescription data, diagnosis data, and other health data associated with one or more patients. As shown, the covered entity computing system 108 may include a network interface 159, a processing circuit 160, and a Rx and Mx data record repository 164. In some embodiments, the covered entity computing system 108 may include an input/output circuit (e.g., similar to the input/output circuit 180).

The network interface 159 is structured to establish connections with the provider computing system 104 by way of the network 118. The network interface 159 includes program logic and/or hardware-based components that connect the covered entity computing system 108 to the network 118. For example, the network interface 159 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 159 includes the hardware and machine-readable media structured to support communication over multiple channels of data communication (e.g., wireless, Bluetooth, near-field communication (NFC). In some embodiments, the network interface 159 includes cryptography logic and capabilities to establish a secure communications session.

The processing circuit 160, as shown, comprises a memory 168, a processor 170, a data matching circuit 172, and a deidentification circuit 174. The memory 168 includes one or more memory devices (e.g., RAM, NVRAM, ROM, flash memory, hard disk storage, etc.) that store data and/or computer code for facilitating the various processes described herein. That is, in operation and use, the memory 168 stores at least portions of instructions and data for execution by the processor 170 to control the processing circuit 160. The memory 168 may be or include tangible, non-transient volatile memory and/or non-volatile memory. The processor 170 may be implemented as a general-purpose processor, an application specific integrated circuit (ASIC), one or more field programmable gate array (FPGAs), a digital signal processor (DSP), a group of processing components or other suitable electronic processing components.

The data matching circuit 172 is structured and/or configured to receive the data record requests from the provider computing system 104 including any additional data for which matching data records are sought (e.g., consumer data, HCP data, etc.) and determine the matching data records. For instance, the data matching circuit 172 may receive a data record request including medical product data (e.g., a list of medical products) for which matching data records are sought. The data matching circuit 172 may then search or query the prescription and medical claims repository 164 for data records that is associated with one or more of the medical products of the medical product data. For example, the data matching circuit 172 may search and return a data record (e.g., an Rx transaction) which is associated with a medical product of the medical product data. In another example, the data matching circuit 172 may search and return data records that matched with consumer data (e.g., demographic data), which may be matched based on identifying data of the data records and the consumer data.

In some embodiments, the covered entity computing system 108 (and more particularly the data matching circuit 172) is structured to aggregate various pieces of internal and external data (e.g., prescription claim (Rx) data, medical claim (Mx) data, media exposure data, HCP data, patient demographics, and the like) based on granularity type.

The deidentification circuit 174 is structured to receive the matched data records and deidentify any identifying data (e.g., PHI or PII) included within the matched data records and corresponding data (e.g., consumer data). To deidentify the identifying data of the matched data records, the deidentification circuit 174 may first determine any identifying data included in the matched data records and then perform one or more operations to remove the associated patient's identity or related private data. In some embodiments, the deidentification circuit 174 may deidentify identifying data of the data records by encrypting the identifying data, tokenizing the identifying data, or by performing some other data masking function.

In some embodiments, all covered entity computing systems 108 from which data records are received by the provider computing system 104 may use the algorithm to generate SMC tokens to provide for consistent SMC tokens across the covered entity computing systems 108. For example, because each covered entity computing system

108 may use the same algorithm to generate SMC tokens, the provider computing system 104 may receive data records, with deidentified PHI or PII, from multiple covered entity computing systems 108. For example, the provider computing system 104 may receive data records including Rx data records from a pharmacy chain covered entity computing system, data records including Mx data records from a medical claims company, data records including clinical data from a medical provider (e.g., a hospital), and government health data records (e.g., Medicare data, Medicaid data, etc.) including national health insurance claims data from a national health insurance provider, each data record including deidentified PHI. Then, the provider computing system 104 may match the various pieces of the received data records based on the deidentified PHI and specifically based on matching SMC tokens.

In some embodiments, the deidentification circuit 174 may deidentify private health information (PHI) or PII of the data record by performing a hash function on the PHI or PII. For example, the deidentification circuit 174 may perform a hash function on the PHI that removes the identity or private information of the patient and returns a hash value in place of the PHI. Example hash functions include, but are not limited to, the mid-square method, string folding, and the like. In some embodiments, all covered entity computing systems from which data records are received by the provider computing system 104 (including the covered entity computing system 108) may use the same hash function to provide for consistent hash values across covered entity computing systems. For example, because each covered entity computing system may use the same hash function (i.e., a hash function that returns the same hash value for the same input), the provider computing system 104 may receive data records, with deidentified PHI, from multiple covered entity computing systems. For example, the provider computing system 104 may receive data records including Rx information from a pharmacy chain covered entity computing system, data records including Mx information from a medical claims company, and data records including clinical information from a medical provider (e.g., a hospital), each set of data records including deidentified PHI. Then, the provider computing system 104 may match the various pieces of received data records based on the deidentified PHI and specifically based on matching hash values. In other embodiments, the provider computing system 104 matches the various pieces of received data records by matching one or more patient demographics or attributes (e.g., same HCP NPI, same date of transaction, same credit card used in both transactions, etc.) to match the data records. In this way, information integrity and usability of the PHI may be maintained while protecting the patients PHI and identity.

Once the deidentification circuit 174 has deidentified the identifying data of the matching data records, the processing circuit 160 and the network interface 159 may be structured to send the data records, including the deidentified PHI, to the provider computing system 104, in response to the data record request. In some embodiments, the covered entity computing system 108 may receive data record requests at specific time intervals and provide the matched data records to the provider computing system 104 at the same time intervals. In this way, the provider computing system 104 may have up-to-date data records and act as a centralized source of reliable data records.

The Rx and Mx data record repository 164 is a repository that receives, stores, and manages various Rx data and/or Mx data associated with the customers or users of the covered entity. To do so, the Rx and Mx data record repository 164 can be structured according to various database types, such as, relational, hierarchical, network, flat, point-in time, and/or object relational. In operation, the Rx and Mx data record repository 164 is configured to store Rx and/or Mx data. In some embodiments, the prescription and medical claims repository 164 is a health data record repository 164 configured to store data records including PHI, Rx data, medical product data, Mx data, and the like. For example, if the covered entity is a medical claims company, the covered entity computing system may include a medical claims database to store medical claims data. In another example, the covered entity computing system 108 may include a national health insurance claims database or an electronic health record database. In some embodiments, the Rx and Mx data record repository 164 is not included in the covered entity computing system 108 but is connected to the covered entity computing system 108 over a covered entity private network or the network 118. In other embodiments, each covered entity computing system 108 may include multiple repositories for each separate type of data record (i.e., a separate repository for Rx data records, EHR data records, and for Mx data records).

Rx data can include transaction data for prescriptions filled by a patient. For example, the Rx data may include medical product data, patient data, PHI, transaction cost/price data, prescribing HCP data, date/time data, and the like. Mx data can include transaction data for medical procedures/treatments filled by a patient. For example, the Mx data may include medical product data, patient data, PHI, transaction cost/price data, prescribing HCP data, date/time data, and the like. EHR data may be similar and include similar data to the Rx and Mx data.

Still referring to FIG. 1, the client computing device 112 can be any type of computing device or computing system. For instance, the client computing device 112 can be one or more of a mobile phone, a tablet computer, a laptop computer, a smart watch, a server computer system, and any other internet-connected device that is capable of running an application. In operation, the client computing device 112 may generate and provide a query to the provider computing system 104 and receive an electronic file, in response. As shown, the client computing device 112 may include a network interface 176, a processing circuit 178, and the input/output circuit 180.

The network interface 176 is structured to establish connections with the provider computing system 104 by way of the network 118. The network interface 176 may be similar to the network interface 126 and include program logic and/or hardware-based components that connect the client computing device 112 to the network 118. For example, the network interface 176 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 176 includes the hardware and machine-readable media structured to support communication over multiple channels of data communication (e.g., wireless, Bluetooth, near-field communication (NFC). In some embodiments, the network interface 176 includes cryptography logic and capabilities to establish a secure communications session.

The processing circuit 178, as shown, may comprise a memory 182, a processor 184, and a user interface generation circuit 185. The memory 182 includes one or more memory devices (e.g., RAM, NVRAM, ROM, flash memory, hard disk storage, etc.) that store data and/or computer code for facilitating the various processes described herein. That is, in operation and use, the memory 182 stores at least portions of instructions and data for execution by the processor 184 to control the processing circuit 178. The memory 182 may be or include tangible, non-transient volatile memory and/or non-volatile memory. The processor 184 may be implemented as a general-purpose processor, an application specific integrated circuit (ASIC), one or more field programmable gate array (FPGAs), a digital signal processor (DSP), a group of processing components or other suitable electronic processing components.

The user interface generation or rendering circuit 185 may be configured to receive a user interface (e.g., a web interface in an HTML file and related files, a downloaded graphical user interface, etc.) from the provider computing system 104 and render the user interface on the client computing device 112 via the I/O circuit 180. In this way, the provider computing system 104 may generate one or more user interfaces and provide the one or more user interfaces to the user interface generation circuit 185 to be rendered on the client computing device 112 (e.g., on a display of the I/O circuit 148 of the user device 112).

The I/O circuit 180 is structured to receive communications from and provide communications to the user of the client computing device 112 (e.g., the user). In this regard, the I/O circuit 180 is structured to exchange data with the processing circuit 178 to provide output to the user and to receive input from the user. As a result, the I/O circuit 180 may include a display that may be manipulated by the application. In some embodiments, the I/O circuit 180 may also include a keyboard, a mouse, a joystick, a touch screen, touch areas, soft keys, a microphone, a speaker, a vibration mechanism, a sensor, an RFID scanner, or other input or output devices described herein.

Still referring to FIG. 1, the one or more national health repositories 120 are each a repository (e.g., database) that receives, stores, and manages various government data records (also referred to as second data records) (e.g., national health insurance (e.g., Medicare, Medicaid) claims information (e.g., Mx and/or Rx claims information), universal health care (e.g., MediFund of Singapore, etc.) or coverage claims information (e.g., Mx and/or Rx), and the like. Further, the government data records may include location information (e.g., zip code, country, city, state), medical product information, national health care statistics (e.g., Rx is from Medicare part A, Medicare part B, Medicare part C, Medicare part D, etc.), HCP information (e.g., NPI of the HCP who prescribed a specific Mx or Rx,), deidentified PHI, and the like.

The national health repository 120 can be structured according to various database types, such as, relational, hierarchical, network, flat, point-in time, and/or object relational. In operation, the national health repository 120 is configured to store, manage, and provide government data records such as national health insurance Rx claims information, national health insurance Mx claims information, and the like. In some embodiments, the one or more national health repositories 120 are each operated by a computing system associated with a government healthcare agency (e.g., the Center for Medicare & Medicaid Services (CMS)). In this regard, the government data records may include a first portion associated with Rx claims information and a second portion associated with Mx claims information. In other embodiments, the national health repositories 120 are each a part of the covered entity computing systems 108.

Further, the government data records may include location information (e.g., zip code, country, city, state), medical product information, national health care statistics (e.g., Rx is from Medicare part A, Medicare part B, Medicare part C, Medicare part D, etc.), HCP information (e.g., NPI of the HCP who prescribed a specific Mx or Rx,), deidentified PHI, and the like.

Referring now to FIGS. 2A-2B, a method 200 of generating a first or original set of projected data records and querying the first set projected data records is shown, according to an example embodiment. Method 200 can be carried out by the system 100 of FIG. 1. More particularly, the method 200 can be carried out by the processing circuit 128 of the provider computing system 104 and through communication with the covered entity computing system 108, and the client computing device 112.

Method 200 commences at step 204 at which the provider computing system 104 generates a data record request. As described herein, the data record request may be generated and populated to include various types of data such as HCP data, consumer data, medical product data, and a timeframe. In some embodiments, the provider computing system 104 may receive or retrieve each various type of data (e.g., retrieve HCP data from an HCP repository (not shown), retrieve consumer data, etc.) prior to step 204. The data record request may request data records (e.g., health data records, Rx records, Mx records, etc.) that are associated with or matches the data included in the data record request.

In some embodiments, at step 204, the provider computing system 104 may generate multiple data record requests. For example, the provider computing system 104 may generate a data record request for each covered entity computing system 108 from which data records are sought. In other embodiments, the provider computing system 104 may generate a single, reused, data record request that is provided to each covered entity computing system 108 from which data records are sought. In one example, the provider computing system 104 may generate a first data record request for all data records associated with a first medical product and within a specific timeframe; and a second data record request for all data records associated with a specific diagnosis code and within a specific timeframe.

Additionally, at step 204, the provider computing system 104 may generate the data record request, at a specific time interval or rate (e.g., once a day, once a week, once a month, every 5 minutes, etc.). In some embodiments, the specific time interval or rate at which the data record request is generated determines the specific timeframe of the data record request. For instance, the provider computing system 104 may generate a data record request at a weekly time interval. As a result, the data record request may be for the timeframe of Jan. 1, 2021-Jan. 7, 2021, and the second data record request may be for the timeframe of Jan. 8, 2021-Jan. 14, 2021. In other examples, the timeframes may overlap to capture latent data records, and the provider computing system 104 may remove duplicate data records as described further herein.

Once the provider computing system 104 has generated the data record request, the method 200 proceeds to step 208 at which the provider computing system 104 provides the data record request to the one or more covered entity computing systems 108. In some embodiments, the provider computing system 104 may provide the data record request over the network 118 via the network interface 126 to the one or more covered entity computing systems 108.

Once the provider computing system 104 has provided the data record request to the one or more covered entity computing systems, the method 200 proceeds to step 212 at which health data records (also referred to as first data records) are received from the one or more covered entity computing systems 108. The first data records may be received in response to the provider computing system 104 providing the data record request to the one or more covered entity computing systems 108 and may be or include Rx records, Mx records, and other data records described herein. For example, the first data records may be prescription claims (Rx) data records that include deidentified PHI or PII, medical product data, diagnosis data (e.g., a diagnosis code), HCP data (e.g., an NPI of a prescribing HCP), date/time data, facility or health care system location data, and transaction data. In another example, the first data records may be medical claims (Mx) data records that includes deidentified PHI or PII, medical product data, procedure data (e.g., procedure code), diagnosis data (e.g., a diagnosis code), HCP data (e.g., an NPI of a prescribing HCP), date/time data, facility or health care system location data, and transaction data. Further, the received first data records may correspond to or be associated with the HCP data, the consumer data, the timeframe, and/or the medical product data included in the data record request. For example, the first data records received at step 212 may be matched with or include consumer data for each individual consumer of each prescription. For example, each Rx data record may be matched with demographic data associated with the consumer of the prescription. Further, the received first data records may include deidentified PHI or PII, transaction data, date/time data, and medical product data.

In some embodiments, the received first data records may be aggregated based on the granularity type included in the data record request. In one example, the data record request may include or identify the granularity type of "HCP" or "NPI." Accordingly, the first data records received at step 212 may be aggregated by patient such that each first data record is sorted or identifiable by NPI (e.g., each data record is a separate NPI of an HCO or HCP, each separate data record is a separate NPI, etc.). In one example, a data record may be associated with the tokenized NPI "12121212". Then, each part (e.g., a cell) of the data record may include an Rx transaction for the NPI "12121212", an Mx transaction for the NPI "12121212", and so on. In another example, the data record request may include or identify a granularity type of "national" or "country=USA." Accordingly, the first data records received at step 212 may be aggregated such that the data records are each associated with the USA. In one example, a data record may be associated with the location "USA" and a specific timeframe.

In other embodiments, the provider computing system 104 may aggregate the received first data records based on the granularity type. In this regard, it should be understood that each data record of the aggregated data records may be associated with a specific grouping (e.g., a specific patient, a specific HCP or NPI, a specific location, etc.), but may include multiple transactions, prescriptions, diagnoses, procedures, dates, and the like therein. The aggregate data records are aggregated such that multiple records of the first data records (e.g., multiple prescriptions, multiple diagnoses, multiple procedures) associated with a common-denominator (e.g., a specific patient, a specific HCP or NPI, a specific location) are joined into a single aggregate data record of the multiple aggregate data records. Further, as described herein, the aggregate data records may be aggregated such that multiple pieces of consumer data (e.g., age range, 3-digit zip code, zip code, payer type for each transaction (e.g., national health insurance (e.g., Medicare Part A), private insurance, cash), occupation, income range, etc.) associated with a common-denominator (e.g., a specific patient, a specific HCP or NPI, a specific location) are joined into a single record of the aggregate data records. For instance, a single aggregate data record may include a part (e.g., a cell) representing the age range (e.g., 20-29 years old) or other consumer data described herein.

As described herein, the PHI or PII of the first data records may be deidentified, by the one or more covered entity computing systems 108, in a variety of ways including through encryption, tokenization, and use of a hash function. In some embodiments, the one or more covered entity computing systems (e.g., the covered entity computing system 108) may use a consistent form of deidentification such that the same PHI or PII input will return the same hash value or token. For example, if a data record included the name "John Smith," a resulting deidentified hash value may be "1234321." To be consistent, each of the one or more covered entity computing systems, when identifying the name "John Smith," may then return the hash value "123431." By using the same hash function across the one or more covered entity computing systems, the provider computing system 104 can make additional connections between the received data records and generate HCP insights and metric values. Further, less processing power is required by the provider computing system 104 as most of the data record matching is completed by the one or more covered entity computing systems prior to the data records being received by the provider computing system 104.

In some embodiments, at or after step 212, the provider computing system 104 determines if the received first data records includes duplicate data records. To determine if the data records includes duplicate data records, the provider computing system 104 may parse each data record and determine if multiple records have one or more matching or at least partially matching data points. For example, the provider computing system 104 may determine that two data records have the same deidentified name hash value (e.g., "1234321"), the same date/time data, and/or the same medical product data. Then, based on these three matching data points, the provider computing system 104 may determine that the two data records are duplicates. In some embodiments, the provider computing system 104 may determine that multiple data records are duplicates if the date/time data, the deidentified PHI or PII, and the medical product data of each data record being the same. In some embodiments, the provider computing system 104 may determine if the data records includes duplicate data records and deduplicate the data records, prior to aggregating the data records.

If, at or after step 212, the provider computing system 104 determines that the received data records includes duplicate data records (or substantially duplicate data records), the provider computing system 104 may modify the received data records to remove the (substantially) duplicate data records. If the received data records includes multiple dupli-cates, the provider computing system 104 may modify the data records to remove or delete each excess data record leaving only a single copy of the duplicate data records. Alternatively, if the first received data records includes multiple pieces of substantially duplicate data records, the provider computing system 104 may modify the data records to combine each leaving only a single, combined, data record including all the data points of the substantially duplicate data records.

Once the provider computing system 104 has received the first data records, the method 200 proceeds to step 216 at which the provider computing system 104 modifies each first data record. For instance, the provider computing system 104 may further modify each data record to enhance or augment (i.e., add data to) the data record. For example, the provider computing system 104 may determine the data record includes a diagnosis code and/or name. Accordingly, the provider computing system 104 may match the diagnosis code with a diagnosis code repository (not shown) and return a first (primary) diagnosis code class and a second diagnosis code class associated with the diagnosis code. The provider computing system 104 may then add the primary diagnosis code class and the second diagnosis code class to the data record.

In another example, the provider computing system 104 may determine the data record includes a zip3 code, but not a state. Accordingly, the provider computing system 104 may determine a state associated with the zip3 code and add the state to the data record. In another example, the provider computing system 104 may modify the data records to remove data records that are empty (e.g., include null values, are not fully populated, etc.). In another example, the provider computing system may determine that the data records includes an HCP NPI code for a prescribing HCP. Accordingly, the provider computing system 104 may match the HCP NPI with an HCP repository (not shown) and populate the data record with various portions of HCP data (e.g., HCP name, HCP zip code, HCP specialty (e.g., Pedia-trician, Cardiologist, etc.), etc.).

In some embodiments, after receiving and/or modifying the first data records, the provider computing system 104 may store the modified first data records in the master data record repository 130. In some embodiments, the provider computing system 104 may add the modified first data records to the master data record repository 130 to replace the previously stored set of data records.

Once the provider computing system 104 has modified the first data records, the method 200 proceeds to step 220 at which the provider computing systems 104 receives or selects second data records (also referred to as government data records) from the one or more national health reposi-tories 120. The second data records may include medical product information (e.g., NDCs), location information (e.g., zip code for a specific Rx or Mx, state for a specific Rx or Mx, country for a specific Rx or Mx, etc.), deidentified PHI or PII, and/or a timeframe (e.g., Jan. 1, 2022-Jan. 2, 2022) associated with the second data records. In some embodiments, the government data records identifies whether a data record is Rx or Mx information. In other embodiments, the provider computing system 104 receives a first set of government data records that are each a RX record and a second set of government data records that are each an Mx record.

As described herein, the provider computing system 104 may receive multiple sets of first data records (e.g., at step 212) and/or multiple sets of second data records (e.g., at step 220). In some embodiments, the order in which the data records is received may be switched. For instance, at step 212, the provider computing system 104 may receive gov-ernment data records, and at step 220, the provider comput-ing system 104 may receive health data records from the one or more covered entity computing systems 108.

In some embodiments, after receiving the second data records, the provider computing system 104 may modify the second data records (e.g., as described at step 216 with regard to the first data record) and/or store the second data records in the master data record repository 130. In other embodiments, the provider computing system 104 may store the (modified) second data record in another repository (e.g., a master second data record repository (not shown), separate from the master data record repository 130 in which the modified first data records are stored.

Once the provider computing system 104 has received the second data records, the method 200 proceeds to step 224 at which the provider computing system 104 selects or receives one or more digital projection models from the projection model repository 134. In some embodiments, the provider computing system 104 may select one or more digital projection models based on the first data records and/or the second data records. For example, the provider computing system 104 may select a first digital projection model from the projection model repository 134 based on the volume of the first data records and/or the second data records information (e.g., number of unique Rx data records, number of unique Mx data records, number of total first data records, number of total second data records, etc.). Because different digital projection models have different use cases, the provider computing system 104 may select, at step 224, the digital projection model that is best suited for the data set. For instance, prior to step 224, the provider computing system 104 may determine the availability and quality of the received data records. Then, at step 224, the provider computing system 104 may select specific models from the projection model repository 134 based on the availability and quality of the received data records. In one example, the provider computing system 104 may determine the received second data records are of poor quality (e.g., is outdated, is low volume, etc.) and select a projection model that only utilizes the first data records. In another example, the provider computing system 104 may determine both sets of data records are high quality and available. As a result, the provider computing system 104 may select a projection model that utilizes the first data records and the second data records.

In some embodiments, at step 224, the provider computing system 104 may select or receive each digital projection model included within the projection model repository 134. For instance, the provider computing system 104 may select a first digital projection model, a second digital projection model, and a third projection model. In some embodiments, the provider computing system 104 may select a first digital projection model from the projection model repository 134 based on the first data records, and the provider computing system 104 may select a second digital projection model from the digital projection model repository 134 based on the second data records.

Once the provider computing system 104 has selected at least one digital projection model, the method 200 proceeds to step 228 at which the provider computing system 104 generates a first set of projected data records based on at least one of the first data records or the second data records using the selected projection model. As described herein, the digital projection models are models (e.g., machine-learning (ML) models, statistical models, etc.) used to determine digitally projected data records (i.e., total projected prescription counts) based on the known values (e.g., the first data records, the second data records, etc.). In some embodiments, the digital projection models are ML models that utilize a feature data set to determine digitally projected data records. The feature data set may include the first data records, the second data records, the HCP data, the consumer data, location data (e.g., of the HCP data) and/or other data described herein. Each set of projected data records may include multiple digitally projected values that are each associated with a different specific location. In some embodiments, the provider computing system 104 may generate multiple sets of projected data records at step 228.

In some embodiments, each set of projected data records may include multiple digitally projected values that are each associated with a specific prescriber or HCO (e.g., HCP). For instance, a set of projected data records may include a first digitally projected value that is associated with (i.e., projected specifically for) a first HCP or HCO (as identified by NPI), a second projected value that is associated with (i.e., projected specifically for) the first HCP or HCO, and so on. In this regard, each digitally projected value of the set of digitally projected records is associated with the correlated NPI.

In some embodiments, each set of projected data records may be associated with a specific medical product and a location or country (e.g., the USA). Then, each digitally projected value of the set of projected data records may be associated with a specific timeframe. For instance, a set of projected data records may include a first digitally projected value that is associated with (i.e., projected specifically for) a first country (e.g., the USA), a first medical product (e.g., drug X), and a first timeframe (e.g., May 2021); a second projected value that is associated with (i.e., projected specifically for) the first country, the first medical product, and a second timeframe (e.g., June 2021); and so on In some embodiments, the provider computing system 104 may determine a set of projected data records for multiple dates/times (e.g., day, month, year, week), for each medical product, and for each data record type (e.g., Mx or Rx). For instance, the provider computing system 104 may determine a first set projected data records for a first month, a first data record type, and a first medical product; a second set of projected data records for a second month, a second data record type and the first medical product; a third set of projected data records for a second month, the first data record type, and a second medical product; and so on. In some embodiments, the provider computing system 104 may generate a first set of projected data records based on the second data records using the selected digital projection model and a second set of projected data records based on the second data records and the modified first data records using the digital projection model. In other embodiments, the provider computing system 104 may generate a second set of projected data records based on the modified first data records using the digital projection model.

Each projected data record (e.g., each digitally projected value) may be or include a projected number of prescriptions (e.g., Rx or Mx transactions) for a specific date/time or timeframe, a specific medical product, a specific NPI or location, and/a specific data record type (e.g., Mx (in-office dispensed prescriptions claims) or Rx (pharmacy-dispensed prescription claims)). For example, because the one or more covered entity computing systems 112 do not cover or include data records associated with all possible prescriptions, the provider computing system 104 must project the missing portions of the data records. For instance, the covered entity computing systems 112 may include data records associated with 40% of all prescriptions in the United States. As a result, using the digital projection models, the provider computing system 104 may project the remaining 60% of prescriptions by determining the projected data records. Further, the provider computing system 104 may project the prescription numbers for each specific NPI or location (e.g., each HCP or HCO NPI, each zip code, each state, each country, etc.), for each medical product (e.g., Drug X, Vaccine Y, etc.), for each data record type (e.g., number of Mx prescriptions and/or number of Rx prescriptions), and for each specific timeframe or date/time (e.g., for June 2021; for 2021; for Jul. 1, 2022, for the first week of June 2021, etc.). By doing so, the systems and methods described herein and the provider computing system 104 provide a technical improvement to prescription projection systems. For instance, conventional prescription projection systems only consider Rx prescriptions and do not utilize or project Mx prescriptions. While this can be suitable for certain medical products, some medical products are primarily in-office dispensed (e.g., prescribed as Mx prescriptions (e.g., Intravenous (IV) fluids, Vaccines, etc.)). As a result, conventional prescription projection systems typically cannot accurately project prescription numbers for certain medical products. In comparison, the present systems and methods project the prescription numbers for each specific data record type including Mx prescriptions. By doing so, the present systems and methods more accurately project total prescription numbers for medical products and provide more usable and accurate digitally projected values.

In some embodiments, the provider computing system 104 may generate a set of projected data records and use the set of projected data records to determine another, summed, set of projected data records. For example, the provider computing system 104 may determine a set of projected data records that is associated with a specific medical product, a specific timeframe (e.g., the month of May 2021), a specification location (e.g., the zip code 53032), and a specific data record type (e.g., Rx). In this regard, each projected data record may be associated with a specific day of the month of May 2021 (e.g., a first digitally projected value associated with May 1, 2021; a second digitally projected value associated with May 2, 2021; and so on). Then, to determine a summed projected data record for May 2021, the provider computing system 104 may sum the set of projected data records by adding each digitally projected value.

In another example, the provider computing system 104 may generate a first set of projected data records (e.g., with a data record type of Rx) and a second set of projected data records (e.g., with a data record type of Mx). Then, for matching HCPs (e.g., based on NPI), the provider computing system 104 may combine or sum one or more of the digitally projected values of the first set of projected data records and the second set of projected data records to generate a third set of projected data records. In this regard, the Mx values and Rx values may be projected separately but combined to generate total prescription counts for HCPs and medical products.

In another example, the provider computing system 104 may combine or add one or more pieces of the projected data records to generate a second set of digitally projected data records. For instance, a specific location (e.g., the zip code 53209) may include four separate HCPs (as indicated by the HCP data). Accordingly, the provider computing system 104 may generate a first set of projected data records including a first digitally projected value associated with the first HCP, a second digitally projected value associated with the second HCP, a third digitally projected value associated with the third HCP, and a fourth digitally projected value associated with the fourth HCP. Next, the provider computing system 104 may combine or add the four digitally projected values to generate a fifth digitally projected value associated with the specific location (e.g., the zip code 53209). This process may be repeated for each specific location (e.g., each zip code, each state, each country, etc.). In this regard, the provider computing system 104 may add or combine (also referred to as roll-up) one or more of the digitally projected values of the first set of projected data records to generate a second set of digitally projected data records. The first set of projected data records may be associated with a first granularity or aggregation type (e.g., HCP), whereas the second set of projected data records may be associated with a second granularity or aggregation type (e.g., zip code). This process may be repeated until reaching the national level. For instance, the provider computing system 104 may combine certain combinations of the first set of projected data records associated with HCPs to generate the second set of projected data records associated with zip codes. Next, the provider computing system 104 may combine certain combinations of the second set of projected data records associated with zip codes to generate a third set of projected data records associated with states. Further, the provider computing system 104 may combine certain combinations of the third set of projected data records associated with states to generate a fourth set of projected data records associated with countries.

By combining digitally projected values to generate additional sets of digitally projected values (i.e., rolling-up the digitally projected values), the provider computing system 104 and the method 200 provide a technical solution to the technical problem of increasing granularity in data records while reducing computational cost. For instance, because the provider computing system 104 generates additional sets of digitally projected values based on a set of digitally projected values with a higher granularity, the present systems and methods provide for increased efficiency and computational speed. For instance, convention systems and methods which perform individual projections at each level of data can be computationally expensive, especially for large datasets or complex models. For instance, building and maintaining separate projection models for each level or granularity of data can be computationally complex and time-consuming to perform. In comparison, because the present systems and methods perform a projection at the highest level of granularity (e.g., HCP-level) and then roll-up the data, the present systems and methods reduce dimensionality allowing for faster calculations, faster computational speed, and requiring less processing power overall. Further, by rolling-up the data, the present systems and methods provide for a more comprehensive model that incorporates information from all levels, reducing overall complexity and maintenance burdens. Likewise, separate projections at each level can be susceptible to individual errors and noise. Instead, because the present systems and methods roll-up the projections to generate additional sets of values, the present systems and methods provide for improved accuracy and reduced variance across levels which smooths out fluctuations in the data and leads to more accurate projections overall.

In some embodiments, at or after step 228, the provider computing system 104 may determine multiple sets of projected data records using one or more of the digital projection models within the projection model repository 134. For instance, the projection model repository 134 may include a first projection model (e.g., a binary classification projection/forecasting model), a second projection model (e.g., a CNN model), and a third projection model (e.g., a linear regression model). As a result, the provider computing system 104 may determine a first set of projected data records using the first digital projection model, a second set of projected data records using the second digital projection model, and a third set of projected data records using the third digital projection model. Then, the provider computing system 104 may determine a confidence score or value, a lower bound value, and/or a higher bound value for each set of projected data records. Then, the provider computing system 104 may rank each of the sets of projected data records (e.g., based on the respective confidence score, based on a lower bound value, based on a higher bound value) and select one of the sets of projected data records (e.g., the highest confidence score that is above the lower bound value and below the higher bound value, the highest confidence score, etc.).

In this regard, at step 228, the provider computing system 104 may modify the three sets of data records to remove the other sets (e.g., the unselected set of projected data records) to select a final set of data records based on the rank of each set of projected data records. For instance, the provider computing system 104 may determine a first set of projected data records, a second set of projected data records, and a third set of projected data records, using a separate digital projection model for each set. Then, the provider computing system 104 may rank each respective set of projected data records. Then, based on the rankings, the provider computing system 104 may select the final set of projected data records.

Once the provider computing system 104 has generated the (final) set of projected data records, the method 200 proceed to step 232 at which the provider computing system 104 stores the projected data records in one of the projected data record repositories 132. In some embodiments, the provider computing system 104 may include a separate projected data record repository 132 for each unique form of the projected data records (e.g., a first projected data record repository 132 for projected data records of drug x, the data record type of Rx, and the granularity type of HCP or NPI; a second projected data record repository 132 for projected data records of drug y, the data record type of Mx, and the granularity type of location, State; etc.). Then, at step 232, the provider computing system 104 may add the set of projected data records to the corresponding projected data record repository 132.

Once the provider computing system 104 has stored the set of projected data records in the projected data record repository 132, the method 200 proceeds to step 236 at which the provider computing system 104 receives a query including one or more configuration properties. In some embodiments, the query may be received from the client computing device 112. As described herein, the query may be designed by the user via the client computing device 112 and provided to the provider computing system 104 for cleaning and generation. For instance, the provider computing system 104 may generate a query page (also referred to as a query-designer or builder page, such as the first query page 400 or the second query page 700) and provide the query page to the client computing device 112 for rendering and display thereon. Through interaction with the query page, the user of the client computing device 112 may design the query and provide the query to the provider computing system 104. The query may include multiple configuration properties (e.g., a first configuration property, a second configuration property, a third configuration property, etc.) and one or more operators, as will be described further herein.

In some embodiments, the query may be received in or as a part of an electronic file generation request. The electronic file generation request may further include a recipient address for the electronic file, a file type (e.g., PDF file, Excel® file, CSV file, etc.), of the electronic file, one or more statistical values to generate, and/or a date or time on which the electronic file is to be generated. For instance, at step 236, the provider computing system 104 may receive an electronic file generation request. The electronic file generation request may include a recipient address (e.g., person1@gmail.com), a file type (e.g., PDF file), the query, and the date Jul. 1, 2021.

In some embodiments, after receiving the initial query from the client computing device 112 (e.g., at or after step 236), the provider computing system 104 may clean and transform the initial query and generate a final query. For instance, in response to receiving the initial query, the provider computing system 104 may modify (i.e., translate) the query to a specific query or data query language (e.g., American National Standards Institute (ANSI) Structured Query Language (SQL), Scala API, etc.). In some embodiments, the specific query or data query language may be based on the projected data record repositories 132. For example, in response to projected data record repositories 132 being relational databases, the provider computing system 104 may modify or standardize (i.e., translate) the initial query to the SQL. In another example, in response to the projected data record repositories 132 being an Amazon Athena service instance, the provider computing system 104 may modify or standardize the initial query to the SQL. In another example, in response to the projected data record repositories 132 being an Amazon Simple Storage Service® (S3) Bucket, the provider computing system 104 may modify or standardize the initial query to the Java programming language. In some embodiments, to clean the initial query, the provider computing system 104 may remove or replace specific characters or expressions. For instance, the provider computing system 104 may replace the character '=' in the expression "age=25" with the character '=='. In another example, the provider computing system 104 may replace the term age in the expression "age=25" with the term "age_c". In other examples, the provider computing system 104 may replace a list of medical products (e.g., Drug X, Drug Y, Drug Z, etc.) with a configuration property representing each medical property and the operator "OR" between each (e.g., "(Drug X OR Drug Y OR Drug Z)")

In some embodiments, after receiving the query, the provider computing system 104 may store the query (e.g., within a query repository (not shown)) and/or generate a query file. The query file may be a specific file type (e.g., Excel file, PDF file, CSV File, etc.) and may be provided to the client computing device 112 by the provider computing system 104. For instance, the provider computing system 104 may generate a query file including a representation of the query (e.g., the configuration properties and/or operators used in the query) and provide the query file to the client computing device 112. In this regard, the user of the client computing device 112 may then replicate the same query, based on the query file.

Once the provider computing system 104 has received the query from the client computing device 112, the method 200 proceeds to step 240 at which the provider computing system 104 (and more particularly the processing circuit 128) executes the (final) query on the corresponding projected data record repositories 132 to select/retrieve or receive at least a portion of the projected data records stored in the projected data record repository 132. For instance, at step 236, the provider computing system 104 may provide the (final) query to the projected data record repository 132 which may then retrieve the matching or resulting projected data records from therein. In another example, the provider computing system 104 (and more particularly the processing circuit 128) may parse the projected data record repository 132 based on the query and select or retrieve the matching or resulting projected data records.

As described herein, the projected data records selected or received from the projected data record repository 132 may match or satisfy the query. In other words, the selected data records may match or meet the configuration propertie(s) and the operator(s) of the query. For instance, the query may include a first configuration property (e.g., Drug X) and a second configuration property (e.g., Mx data), with the operator "AND" between the first configuration property and the second configuration property (i.e., "(Drug X AND Mx data)"). In response to receiving the query, the provider computing system 104 may execute the query and select or receive each projected data record from the projected data record repository 132 that is associated with Drug X and is the data record type of Mx.

In some embodiments, executing the query may include multiple steps or stages. For instance, at a first step, the provider computing system 104 may execute the query and select corresponding projected data record repository 132 to retrieve the data records from (e.g., the projected data record repository 132 for drug x and the granularity type of HCPs). Then, at a second step, the provider computing system 104 may select the corresponding projected data records and remove each data record that does not have a specific data record type (e.g., Mx).

Once the provider computing system 104 has executed the query and selected the portion of the data records from the projected data record repository 132, the method 200 proceeds to step 244 at which the provider computing system 104 generates an electronic file including the selected portion of the projected data records.

The electronic file may be generated as a specific file type as set by the client computing device 112 in the electronic file generation request. For example, the electronic file may be generated as a CSV file, an Excel File (XLSX file), an XML file, a JSON file, and the like. By allowing the client computing device 112 to decide and set the specific file type of the electronic file in the electronic file generation request and not generating the electronic file as one specific file type, the provider computing system 104 may provide for improved shareability of the electronic file as well as use less processing power and memory. For example, in situations where the electronic file is only generated as a specific, non-dynamic, file type, third-party computing systems and recipient computing devices (e.g., the client computing device 112) may have to perform additional file modification and conversion or request the provider computing system 104 to do so, which requires additional processing power, memory (to keep two files), and time. In comparison, the system 100 and the provider computing system 104 allow the user to specify the file type of the electronic file through the electronic file generation request. Accordingly, the user, via the client computing device 112, can specify the wanted file type the first time and the provider computing system 104 will generate the electronic as the specified file type. As a result, no additional file modification or conversion is required reducing processing power usage, memory usage, and overall processing time for the provider computing system 104.

Once the provider computing system 104 has generated the electronic file, the method 200 proceeds to step 248 at which the electronic file is provided or output. In some embodiments, the electronic file is output to the file destination address of the electronic file generation request. The file destination address may be any type of address or destination (e.g., IP address, web address, email address, file transfer protocol (FTP) address, and the like) to which the electronic file may be electronically transmitted or provided. In one example, the file destination address may be another server or circuit of the provider computing system 104 that is configured to receive the electronic file (e.g., Veeva Nitro®). In another example, the file destination address may be a web address of the Amazon S3® cloud storage web service. In another example, the file destination address may be the IP address of the client computing device 112 and the electronic file may be provided to the client computing device 112.

Figure 3B:
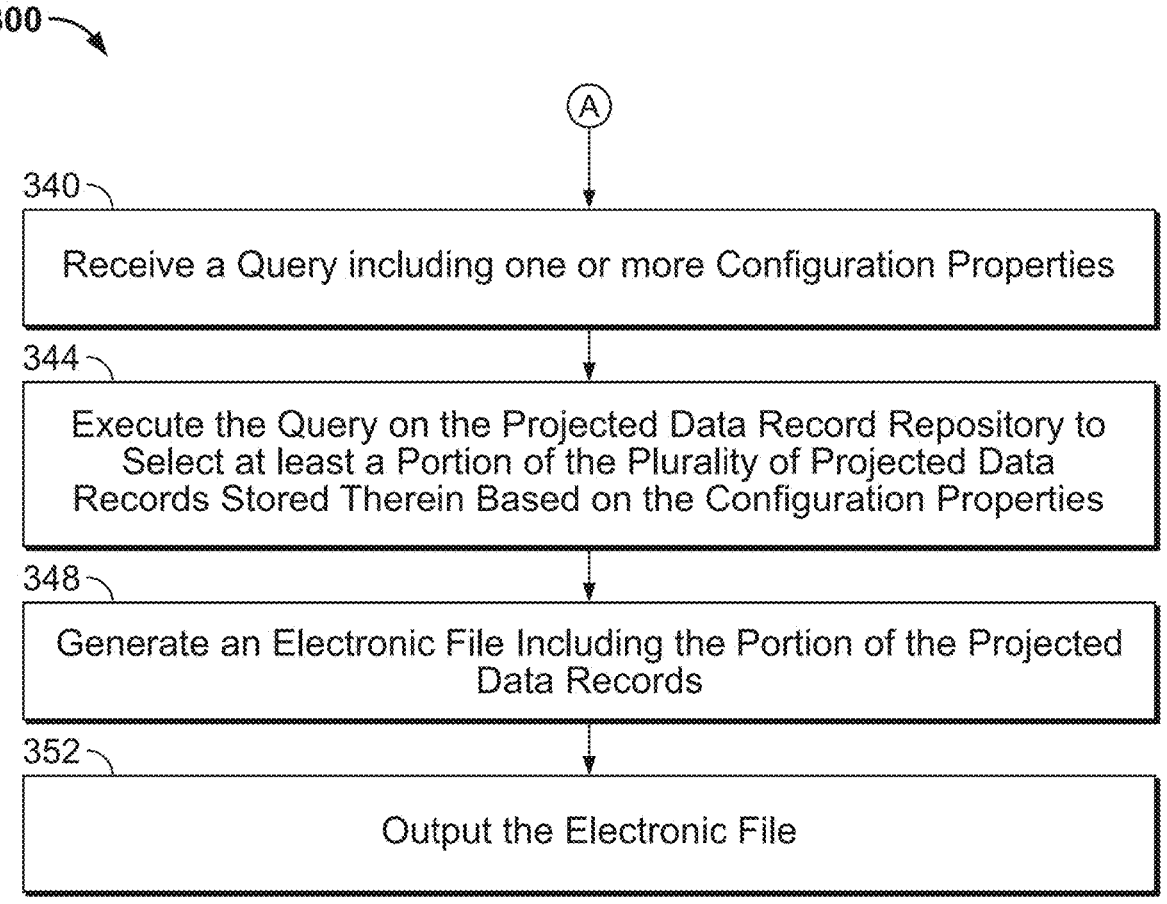

Referring now to FIGS. 3A-3B, a method 300 of generating a second or new set of projected data records and querying the new set projected data records is shown, according to an example embodiment. While different overall, it should be understood that any steps or discussion of the method 300 may be applied or included within the method 200 or the method 800 and vice versa, and that such combinations are included within the scope of the present disclosure. For example, the method 200 may include any of the steps 304-352 or steps 804-872 after or before any steps included in the method 200, and the method 300 may include any of the steps 204-248 or steps 804-872 after or before any of the steps included in the method 300. Likewise, the method 800 may include any of the steps 204-248 or steps 304-352 before or after any steps included in the method 800. In a specific example, the provider computing system 104 may perform method 200 to determine the original or first set of projected records). Then, the method 300 may be performed by the provider computing system 104 in response and then perform the method 300 to determine a new set of projected data records. Method 300 can be carried out by the system of FIG. 1. More particularly, the method 300 can be carried out by the processing circuit 128 of the provider computing system 104 and through communication with the client computing devices 112.

Method 300 commences at step 304 at which the provider computing system 104 generates a data record request. Step 304 may be the same as step 204 of the method 200. As described herein, the data record request may be generated and populated to include various types of data such as HCP data, consumer data, medical product data, and a timeframe. In some embodiments, the provider computing system 104 may receive or retrieve each various type of data (e.g., retrieve HCP data from an HCP repository (not shown), retrieve consumer data, etc.) prior to step 204. The data record request may request data records (e.g., health data records, Rx records, Mx records, etc.) that are associated with or matches the data included in the data record request.

Once the provider computing system 104 has generated the data record request, the method 300 proceeds to step 308 at which the provider computing system 104 provides the data record request to the one or more covered entity computing systems 108. In some embodiments, the provider computing system 104 may provide the data record request over the network 118 via the network interface 126 to the one or more covered entity computing systems 108.

Once the provider computing system 104 has provided the data record request to the one or more covered entity computing systems, the method 300 proceeds to step 312 at which health data records (also referred to as first data records) are received from the one or more covered entity computing systems 108. The step 312 may be the same as the step 212 of the method 200. The first data records may be received in response to the provider computing system 104 providing the data record request to the one or more covered entity computing systems 108 and may be or include Rx records, Mx records, and other data records described herein. For example, the first data records may be prescription claims (Rx) data records that include deidentified PHI or PII, medical product data, diagnosis data (e.g., a diagnosis code), HCP data (e.g., an NPI of a prescribing HCP), date/time data, facility or health care system location data, and transaction data. In another example, the first data records may be medical claims (Mx) data records that includes deidentified PHI, medical product data, procedure data (e.g., procedure code), diagnosis data (e.g., a diagnosis code), HCP data (e.g., an NPI of a prescribing HCP), date/time data, facility or health care system location data, and transaction data.

As described herein, the PHI or PII of the first data records may be deidentified, by the one or more covered entity computing systems 108, in a variety of ways including through encryption, tokenization, and use of a hash function. In some embodiments, the one or more covered entity computing systems (e.g., the covered entity computing system 108) may use a consistent form of deidentification such that the same PHI or PII input will return the same hash value or token. For example, if a data record included the name "John Smith," a resulting deidentified hash value may be "1234321." To be consistent, each of the one or more covered entity computing systems, when identifying the name "John Smith," may then return the hash value "123431." By using the same hash function across the one or more covered entity computing systems, the provider computing system 104 can make additional connections between the received data records and generate HCP insights and metric values. Further, less processing power is required by the provider computing system 104 as most of the data record matching is completed by the one or more covered entity computing systems prior to the data records being received by the provider computing system 104.

Once the provider computing system 104 has received the first data records, the method 300 proceeds to step 316 at which the provider computing system 104 modifies each first data record. Step 316 may be the same as the step 216 of the method 200. For instance, the provider computing system 104 may further modify each data record to enhance or augment (i.e., add data to) the data record. In one example, the provider computing system 104 may determine the data record includes a diagnosis code and/or name. Accordingly, the provider computing system 104 may match the diagnosis code with a diagnosis code repository (not shown) and return a first (primary) diagnosis code class and a second diagnosis code class associated with the diagnosis code. The provider computing system 104 may then add the primary diagnosis code class and the second diagnosis code class to the data record.

In another example, the provider computing system 104 may determine the data record includes a zip3 code, but not a state. Accordingly, the provider computing system 104 may determine a state associated with the zip3 code and add the state to the data record. In another example, the provider computing system 104 may modify the data records to remove data records that are empty (e.g., include null values, are not fully populated, etc.). In another example, the provider computing system may determine that the data records includes an HCP NPI code for a prescribing HCP. Accordingly, the provider computing system 104 may match the HCP NPI with an HCP repository (not shown) and populate the data record with various portions of HCP data (e.g., HCP name, HCP zip code, HCP specialty (e.g., Pediatrician, Cardiologist, etc.), etc.).

In some embodiments, after receiving and/or modifying the first data records, the provider computing system 104 may store the modified first data records in the master data record repository 130. In some embodiments, the provider computing system 104 may add the modified first data records to the master data record repository 130 to replace the previously stored set of data records.

Once the provider computing system 104 has modified the first data records, the method 300 proceeds to step 320 at which the provider computing systems 104 receives or selects second data records (also referred to as government data records) from the one or more national health repositories 120. The second data records may include medical product information (e.g., NDCs), location information (e.g., zip code for a specific Rx or Mx, state for a specific Rx or Mx, country for a specific Rx or Mx, etc.), deidentified PHI or PII, and/or a timeframe (e.g., Jan. 1, 2022-Jan. 2, 2022) associated with the second data records. In some embodiments, the government data records identifies whether a data record is Rx or Mx information. In other embodiments, the provider computing system 104 receives a first set of government data records that are each a RX record and a second set of government data records that are each an Mx record.

As described herein, the provider computing system 104 may receive multiple sets of first data records (e.g., at step 312) and/or multiple sets of second data records (e.g., at step 320).

Once the provider computing system 104 has received the second data records, the method 300 proceeds to step 324 at which the provider computing system 104 receives a request to lock or fix a projection model for a set of digitally projected records. In some embodiments, the request may specifically identify the set of digitally projected records (e.g., identify the granularity type and/or the medical product). In other embodiments, the request may identify multiple sets of digitally projected values. In some embodiments, the request may further specify the projection model which is to be utilized when generating the new set of digitally projected values. In some embodiments, the request may be received from the client computing device 112.

In other embodiments, at step 324 the provider computing system 104 may generate a request or file including the digital projection models, quality and volume data associated with the data records, and a text query, and output the request or file to an artificial intelligence (AI) computing system (not shown). The file may further include an application programming interface (API) key. Then, in response, the provider computing system 104 may receive a response file from the AI computing system, which may include an indication or request to lock the projection model.

Once the provider computing system 104 has received the request to fix or lock the projection model, the method 300 proceeds to step 328 at which the provider computing system 104 determines the projection model used to project the identified set of digitally projected records. For instance, as described herein, the provider computing system 104 may query the projected data record repository 132, to retrieve a batch or metadata file associated with the set of digitally projected records. Then, based on the metadata file, the provider computing system 104 may determine the projection model used to generate the set of digitally projected records. In another example, the set of digitally projected records may further include or identify the projection model used (e.g., in each record, in each set of records). Accordingly, the provider computing system 104 may query the projected data record repository 132, to retrieve at least one digitally projected record. Then, based on the at least one record, the provider computing system 104 may determine the projection model used to generate the set of digitally projected records.

In some embodiments, at step 328, the provider computing system 104 may determine the projection model identified in the request to fix the projection model. In some embodiments, at or after step 328, the provider computing system 104 may determine a historical or data-derived correction factor based on the set of digitally projected values and/or previous sets of digitally projected values. As described herein, the projection model is used to project or predict the total number of prescriptions for a specific granularity and medical product based on known data (e.g., the first data records and the second data records). Accordingly, the projection model is not a source of truth and is dependent on the known data. In this regard, the quality and quantity of the known data can have an effect on the quality of the projected data records. Accordingly, the provider computing system 104 may continually update and determine projected data records, as new data is received. In this regard, as the values are modified and updated, the provider computing system 104 may calculate a correction factor based on the previous sets of projected data records of the same type (e.g., same granularity type, same medical product, etc.). The correction factor may be equal to the newest projected value divided by the previously projected value. In another example, the correction factor may be determined by calculating the mean absolute error (MAE) factor based on the sets of digitally projected records. MAE measures the average absolute difference between the projected and actual values; it quantifies the historical error. In some embodiments, the correction factor may be a mean square error (MSE) value, a root mean square error (RMSE) value, a Median absolute error (MAD) value, a Mean Absolute Percentage Error (MAPE), and the like. In some embodiments, the request may identify the specific correction factor to be used.

Once the provider computing system 104 has determined the projection model, the method 300 proceeds to step 332 at which the provider computing system 104 determines a new set of digitally projected records using the determined digital projection model based on the at least one of the modified first set data records or the second set of data records. Step 332 may be similar or the same as step 228 of the method 200. As described herein, the first or original set of digitally projected records may be projected as a specific type (e.g., for a specific granularity, for a specific medical product, etc.) but for a first time frame or temporal window (e.g., the month of June 2021, from June 2021 to June 2022, etc.). Accordingly, the second or new set of digitally projected records may be projected as the same specific type but for a second time frame or temporal window (e.g., the month of July 2021, from July 2021 to July 2022, etc.). Likewise, as compared to projecting multiple sets of values and then selecting a final set (e.g., as described with regard to step 228), the provider computing system 104 may simply utilize the projection model used to project the final set of projected records. In this regard, because each projection model uses different sets of data (e.g., a first model uses the first data records, a second model uses the second data records, a third model uses both the first data records and the second data records, etc.), the provider computing system 104 may generate the projected records based on the first data records and/or the second data records.

As described herein, the projection model is used to project or predict the total number of prescriptions for a specific granularity and medical product based on known data (e.g., the first data records and the second data records). Accordingly, because the known data fluctuates, the projected values generated by the projection model can largely fluctuate over different timeframes. This is further exacerbated by the provider computing system 104 continually selecting the most projection model and projected records with the greatest confidence score. For example, the provider computing system 104 may generate three set of projected values for a specific granularity (e.g., HCP NPI of 11221122), a specific medical product (e.g., drug x), and a specific timeframe (e.g., the month of June 2021). The provider computing system 104 may then determine a confidence score with each and select one of the sets as the final set of projected values based on the confidence score. The final set may have been generated using a first projection model. Then, for the next month's projection (e.g., same granularity, same medical product, month of July 2021), the provider computing system 104 may again generate three sets of projected values and select another final set. The new final set may have been generated using a second projection model. Accordingly, because of all this variation, the values of the first final set and the second final set may greatly vary (e.g., 1,000 Rx projected prescriptions compared to 2,100 Rx projected prescriptions, 50 Mx projected prescriptions compared to 5 Mx projected prescriptions, 1,050 total projected prescriptions (TRx) compared to 2,105 TRx projected prescriptions).

In comparison, the present systems and methods may utilize projection methodology method-locking which provides for more stabile and readily-usable sets of projected data records and a technical improvement to data projection methodologies. For instance, because the systems and methods use multiple projection models to project the data records, the present systems provide for improved data accuracy and reduced bias. For example, combining multiple models can reduce the impact of individual model errors, leading to more accurate predictions. Likewise, by choosing the best-performing model, the present systems and methods can significantly improve the accuracy of the projected data records and reduce bias that might be inherent in any single model. However, once the model is selected and locked, it provides a stable foundation for future projections, reducing the risk of sudden and unpredictable changes. In comparison, typical data projection systems may attempt to create more stable projected data by considering the previously projected value as a true value. This can create inherent bias and inaccuracy in the model, which only grows as future projections are made based on that value, the following value, and so on. In comparison, the present systems and methods only treat actual values as true (e.g., the first data records and the second data records), then select the highest-rated projection model that fits the actual data. Then, the present systems and methods enact a method-lock utilizing that same projection model to generate future predictions, which creates stability in the projections and ensures that projections are comparable over time.

Once the provider computing system 104 has generated the new of projected data records, the method 300 proceed to step 336 at which the provider computing system 104 stores the projected data records in one of the projected data record repositories 132. In some embodiments, the provider computing system 104 may add the new set of projected data records to the same projected data record repository 132 as the original set of projected data records.

Once the provider computing system 104 has stored the set of projected data records in the projected data record repository 132, the method 300 proceeds to step 340 at which the provider computing system 104 receives a query including one or more configuration properties. Step 340 may be similar or the same as step 236 of the method 200. In some embodiments, the query may be received from the client computing device 112. As described herein, the query may be designed by the user via the client computing device 112 and provided to the provider computing system 104 for cleaning and generation. For instance, the provider computing system 104 may generate a query page (also referred to as a query-designer or builder page, such as the first query page 400 or the second query page 700) and provide the query page to the client computing device 112 for rendering and display thereon. Through interaction with the query page, the user of the client computing device 112 may design the query and provide the query to the provider computing system 104. The query may include multiple configuration properties (e.g., a first configuration property, a second configuration property, a third configuration property, etc.) and one or more operators, as will be described further herein. In some embodiments, the query may be received in a file generation request that further includes a specific file type and a file destination address.

Once the provider computing system 104 has received the query from the client computing device 112, the method 300 proceeds to step 344 at which the provider computing system 104 (and more particularly the processing circuit 128) executes the (final) query on the corresponding projected data record repositories 132 to select/retrieve or receive at least a portion of the projected data records stored in the projected data record repository 132. Step 344 may be the same as step 240 of the method 200. For instance, at step 344, the provider computing system 104 may provide the (final) query to the projected data record repository 132 which may then retrieve the matching or resulting projected data records from therein. In another example, the provider computing system 104 (and more particularly the processing circuit 128) may parse the projected data record repository 132 based on the query and select or retrieve the matching or resulting projected data records.

Once the provider computing system 104 has executed the query and selected the portion of the data records from the projected data record repository 132, the method 300 proceeds to step 348 at which the provider computing system 104 generates an electronic file including the selected portion of the projected data records.

Once the provider computing system 104 has generated the electronic file, the method 300 proceeds to step 352 at which the electronic file is provided or output. In some embodiments, the electronic file is output to the file destination address of the electronic file generation request. The file destination address may be any type of address or destination (e.g., IP address, web address, email address, file transfer protocol (FTP) address, and the like) to which the electronic file may be electronically transmitted or provided. In one example, the file destination address may be another server or circuit of the provider computing system 104 that is configured to receive the electronic file (e.g., Veeva Nitro®). In another example, the file destination address may be a web address of the Amazon S3® cloud storage web service. In another example, the file destination address may be the IP address of the client computing device 112 and the electronic file may be provided to the client computing device 112.

Referring now to FIGS. 4A-7D user interfaces shown and displayed to the user of the one or more user computing devices 112 during the method 200 and/or 300 are shown, according to example embodiments. As described herein, the user interfaces of FIGS. 4A-7D may be one or more of web interfaces generated by the provider computing system 104 and rendered by the client computing device 112 as part of a web application or graphical user interfaces downloaded and generated by the client computing device 112 as part of a software application (e.g., a mobile application, etc.). Further, the user interfaces shown on FIGS. 4A-7D allow for communication between the user and the provider computing system 104 via the respective client computing device 112 (specifically via the I/O circuit 180). Through interaction with the various user interfaces, the user may provide user input, feedback, and other data requested by the provider computing system 104. In this regard, it should be understood that each interaction described herein by the user with the user interfaces of FIGS. 4A-7D may be provided to the client computing device 112 and then transmitted to the provider computing system 104 and that each action described herein as occurring to the respective client computing device 112 (e.g., navigating to a certain page, generating a popup, etc.) may be performed by the provider computing system 104.

Figure 4A:
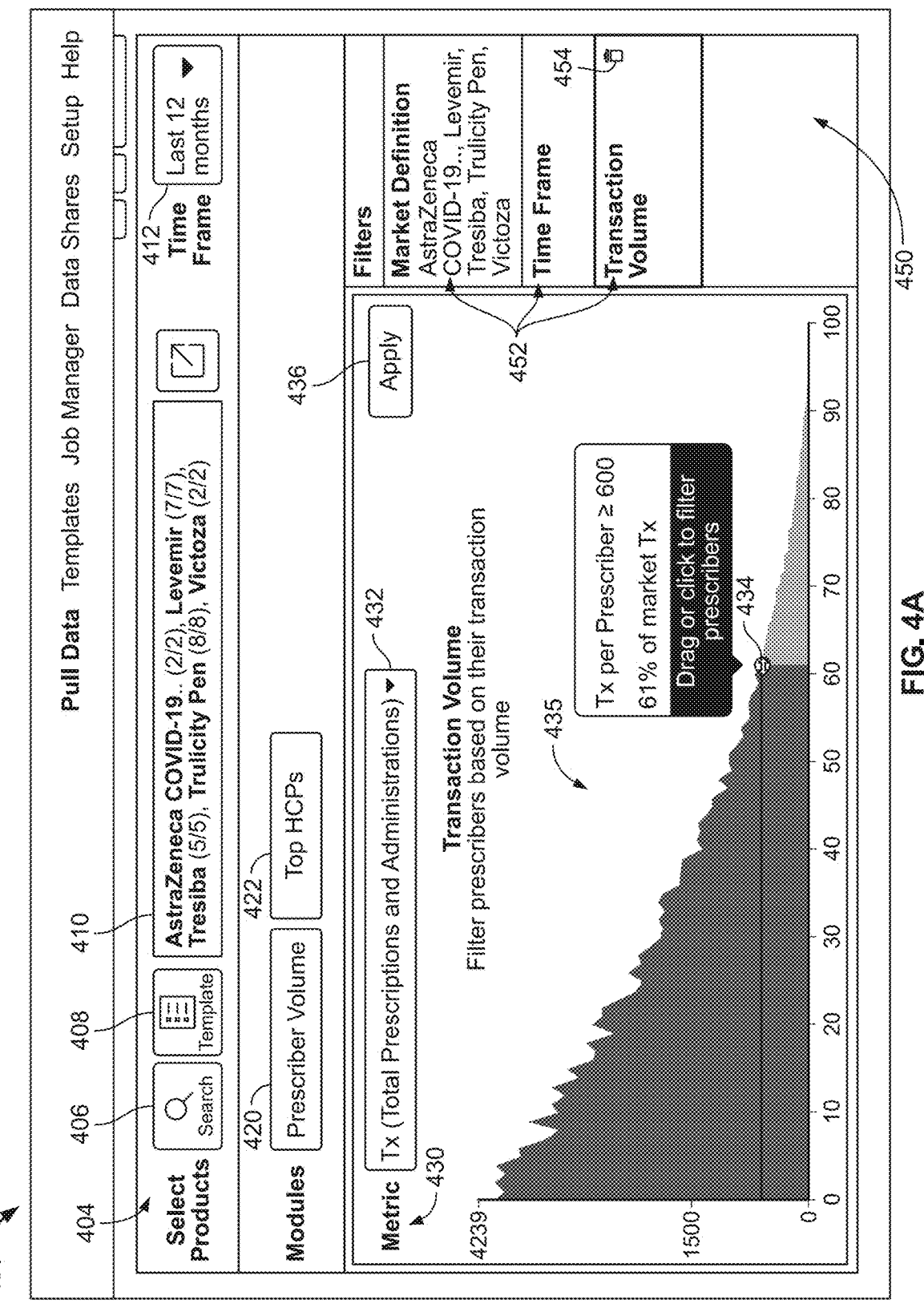
FIGS. 4A-4B are illustrations of some aspects of a user interface generated by the query generation and health data analyzation system of FIG. 1 to receive a query, according to an example embodiment.
Figure 4B:
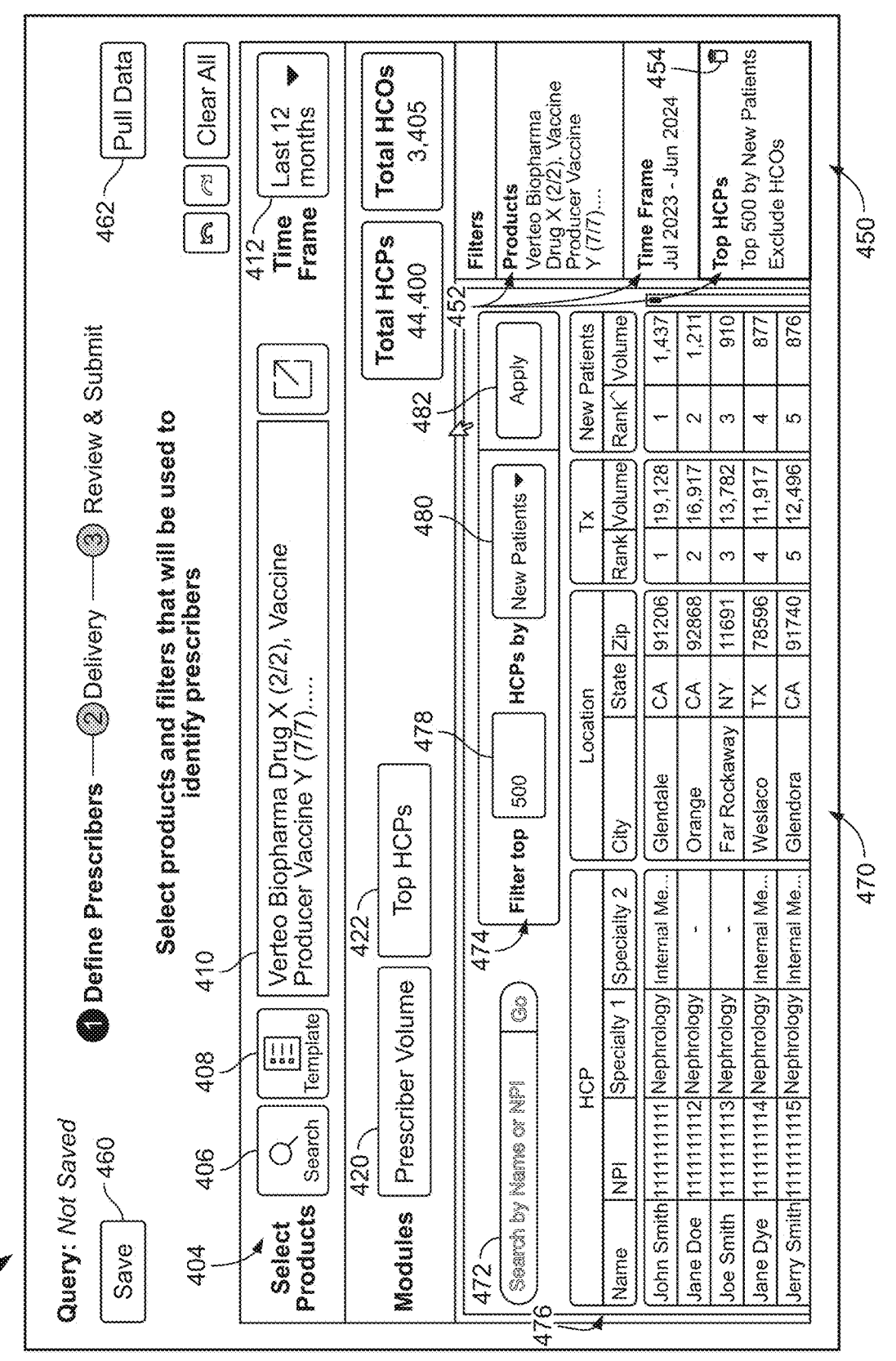

Referring now to FIGS. 4A-4B, a query page 400 (also referred to as the first query page 400), which can be displayed on a display of the I/O circuit 180 of the client computing device 112 is shown. In general, the query page 400 provides the respective client computing device 112 with an interface to design and manage the query for projected data records (e.g., the query in the method 200 and the method 300) and provide the query to the provider computing system 104 for execution. For example, via the query page 400, the user may provide the query including one or more requested configuration properties to the computing device 112, which may provide the initial query to the provider computing system 104 for execution therein. In this regard, the provider computing system 104 may provide medical product data, diagnosis data, procedure data, and the like to the respective client computing device 112 to enable display of the query page 400 on the display of the I/O circuit 180.

As shown, the query page 400 includes a medical product section 404, a timeframe field 412, a first module button 420, a second module button 422, a transaction volume section 430, a filter section 450, and an HCP listing section 470. The medical product section 404 includes the search button 406, the template button 408, and the results display field 410. The search button 406, the template section 408, and the results display field 410 may be interactive fields which provide an interface to define a group or set of medical products (as discussed further with regard to FIG. 6). For instance, in response to selecting the template button 408, the client computing device 112 may be navigated to a medical product group selection page 600 to select and/or define a specific medical product group, which may then be displayed in the display field 410 and included as a configuration property in the query.

The timeframe field 412 may be a drop-down box with multiple options (e.g., last 12 months, last 24 months, last 36 months, etc.) to select the timeframe configuration property which may be included in a generated query. For instance, in response to selecting the option "last 12 months", in the time frame field 412, the client computing device 112 may generate the query to include a configuration property of the timeframe of the last 12 months. Then, in response to receiving the query, the provider computing system 104 may select or query projected data records which is associated with a date/time within the last 12 months. In comparison, in response to selecting the option "last 24 months", in the time frame field 412, the client computing device 112 may generate the query to include a configuration property of the timeframe of the last 24 months. Then, in response to receiving the query, the provider computing system 104 may select or query projected data records which are associated with a date/time within the last 24 months.

The module buttons 420 and 422 may each be selectable buttons that change what is displayed on the query page 400. For instance, in response to a selection of the first module button 420, the client computing device 112 may display the transaction volume section 430 on the query page 400. In comparison, in response to a selection of the second module button 422, the client computing device 112 may display the HCP listing section 470.

The transaction volume section 430 provides an interface to set a configuration property of the projection value volume of a specific HCP. Further, the transaction volume section 430 includes a metric field 432, a draggable or selectable transaction volume button 434, an interactive chart 435 and an apply button 436. The metric field 432 may be a drop-down box with multiple options (e.g., Tx, TRx, TMx) to select the data record type (e.g., Mx, Rx, or Tx (Mx+Rx)) on which the volume is to be included in a configuration property. Likewise, the draggable transaction volume button 434 is a draggable button or field that can be used to interact with the interactive chart 435 and set specific values by moving the button 434. For instance, as shown, the value is set to ≥600 Tx (Rx+Mx). In this regard, the client computing device 112 may generate the query to include a configuration property of greater than or equal to 600 total transactions (for the past 12 months). Accordingly, in response to receiving the request, the provider computing system 104 may query or select projected data records for (e.g., associated with) HCPs or NPIs who have greater than or equal to 600 prescriptions (Rx prescriptions and Mx prescriptions combined) in the last year, as discussed with regard to step 232. In comparison, if the metric field 432 was set to Rx, the provider computing system 104 may query or select projected data records for (e.g., associated with) HCPs or NPIs who have greater than or equal to 600 Rx prescriptions (Rx prescriptions and Mx prescriptions combined) in the last year. To generate the query, the user of the client computing device 112 may select the apply button 436. In response, the client computing device 112 may generate the query including the configuration properties set thereof (e.g., the first configuration property, the second configuration property, and the third configuration property) and provide the query to the provider computing system 104. The provider computing system 104 may then query the projected data records and display it on the query page 400 (e.g., in the interactive chart 435).

Still referring to FIG. 4, the filter section 450 may include multiple filter or configuration property representations 452 including a medical product group filter representation 452, a timeframe filter representation 452, and a transaction volume filter representation 452. Each filter representation 452 may represent a specific filter or configuration property (e.g., a transaction volume filter, a medical product group filter, a timeframe filter, etc.) that is to be included in the query. Likewise, each filter representation 452 may include a delete button 454 that, when selected, removes the filter representation 452 and the filter from being added to the query.

Referring now directly to FIG. 4B, the HCP listing section 472 may provide a line listing of the HCPs with the most transaction volume (e.g., most projected Rx, most projected Mx, most projected TRx, etc.) for the selected medical products. As shown, the HCP listing section 472 includes a search bar 472, a filter top prescriber section 474, and a line listing section 476. The filter top prescriber section 474 may provide the user of the client computing device 112 an interface to filter the top prescribers shown in the line listing section 476 and may generate a filter representation 452.

Figure 5:
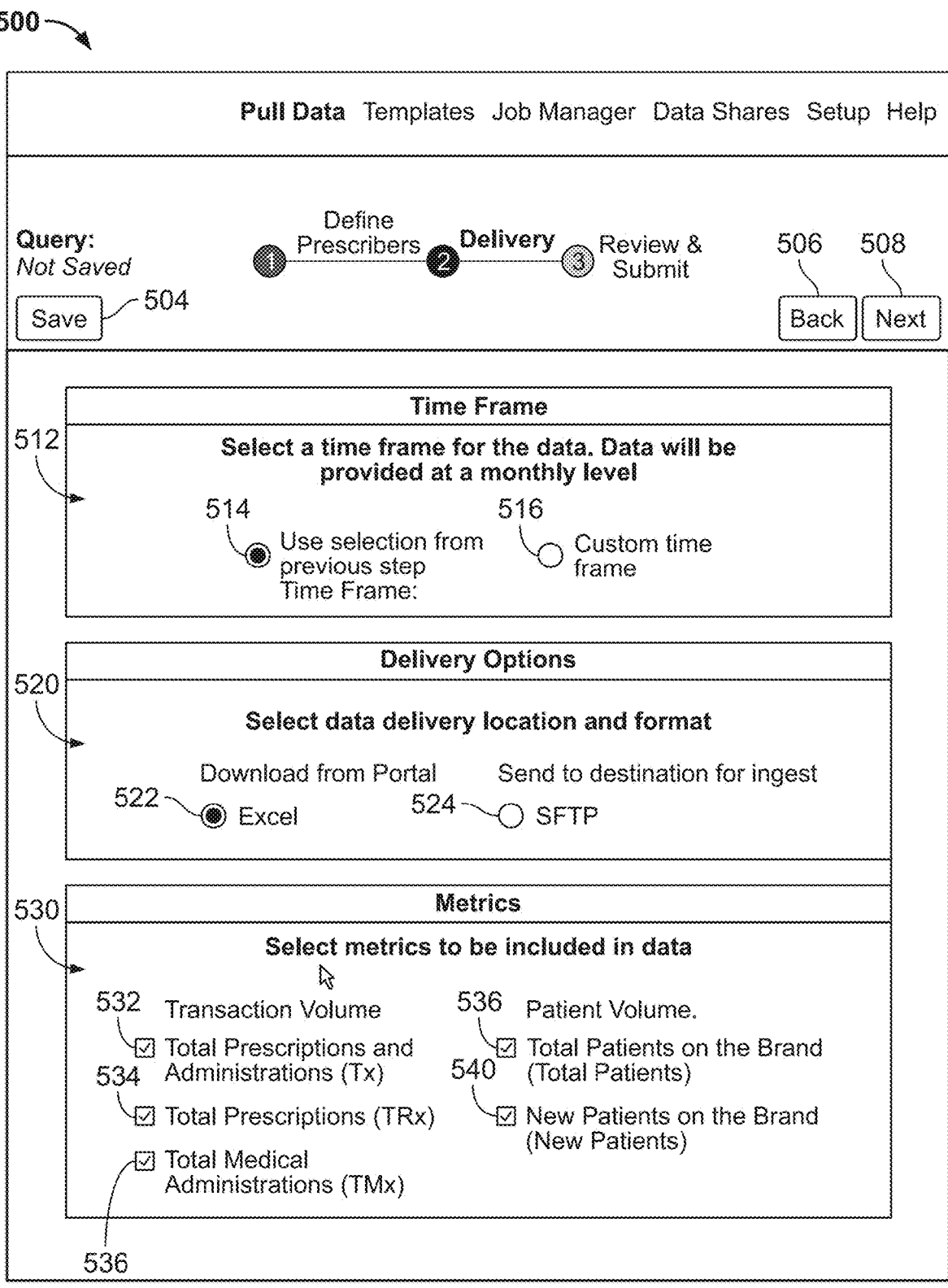
FIG. 5 is an illustration of some aspects of a user interface generated by the query generation and health data analyzation system of FIG. 1 to receive a file generation request, according to an example embodiment.

Referring now to FIG. 5 a delivery page 500, which can be displayed on a display of the I/O circuit 180 of the client computing device 112, is shown. In general, the delivery page 500 provides the user with an interface to generate and provide an electronic file generation request to the provider computing system 104, in combination with the first query page 400 and/or the second query page 700. To access or be navigated to the delivery page 500, the user of the client computing device 112 may navigate to the query page 400, then set their configuration properties and select a next button (not shown). As shown, the delivery page 500 includes a save button 504, a back button 506, a next button 508, a time frame section 512, a delivery options section or menu 520, and a metrics or values section 530.

The save button 504 is a selectable button that, when selected, causes the client computing device 112 to provide the draft electronic file generation request to the provider computing system 104 for storage therein. Likewise, the previous button 506 is a selectable button that, when selected, navigates the client computing device 112 to the query page 400. Similarly, the next button 508 is a selectable button that, when selected, navigates the client computing device 112 to a submission page (not shown) where the details of the electronic file generation request are confirmed and the client computing device 112 receives an indication to generate the electronic file generation request.

The time frame section 512 is a section where the client computing device 112 can set the time frame configuration property of the query of the electronic file generation request. As shown, the time frame section 512 includes a first selectable option 1514 and a second selectable option 516. In operation, the user of the client computing device 112 can select the first selectable option 514 to set the time frame as the selection from the query page 400 (e.g., in the time frame field 412). In comparison, if the second selectable option 516 is selected, the user can set a custom time frame (e.g., last 12 months, last 6 months, Dec. 1, 2023-4/15/2023, etc.).

The delivery options section or menu 520 may include a first delivery option 522 and a second delivery option 524. In operation, the user of the client computing device 112 can select the first selectable option 522 to set a first delivery address for the electronic file generation request or the second selectable option 524 to set a second delivery address for the electronic file generation request.

The metrics section 530 may include multiple checkboxes including a Tx checkbox 532, a TRx checkbox 534, a TMx checkbox 536, a total patients checkbox 538, and new patient starts checkbox 540. In operation, the user of the client computing device 112 can select multiple checkboxes to select the projected data records and the metric values to be returned in the query and included in the electronic file.

Figure 6:
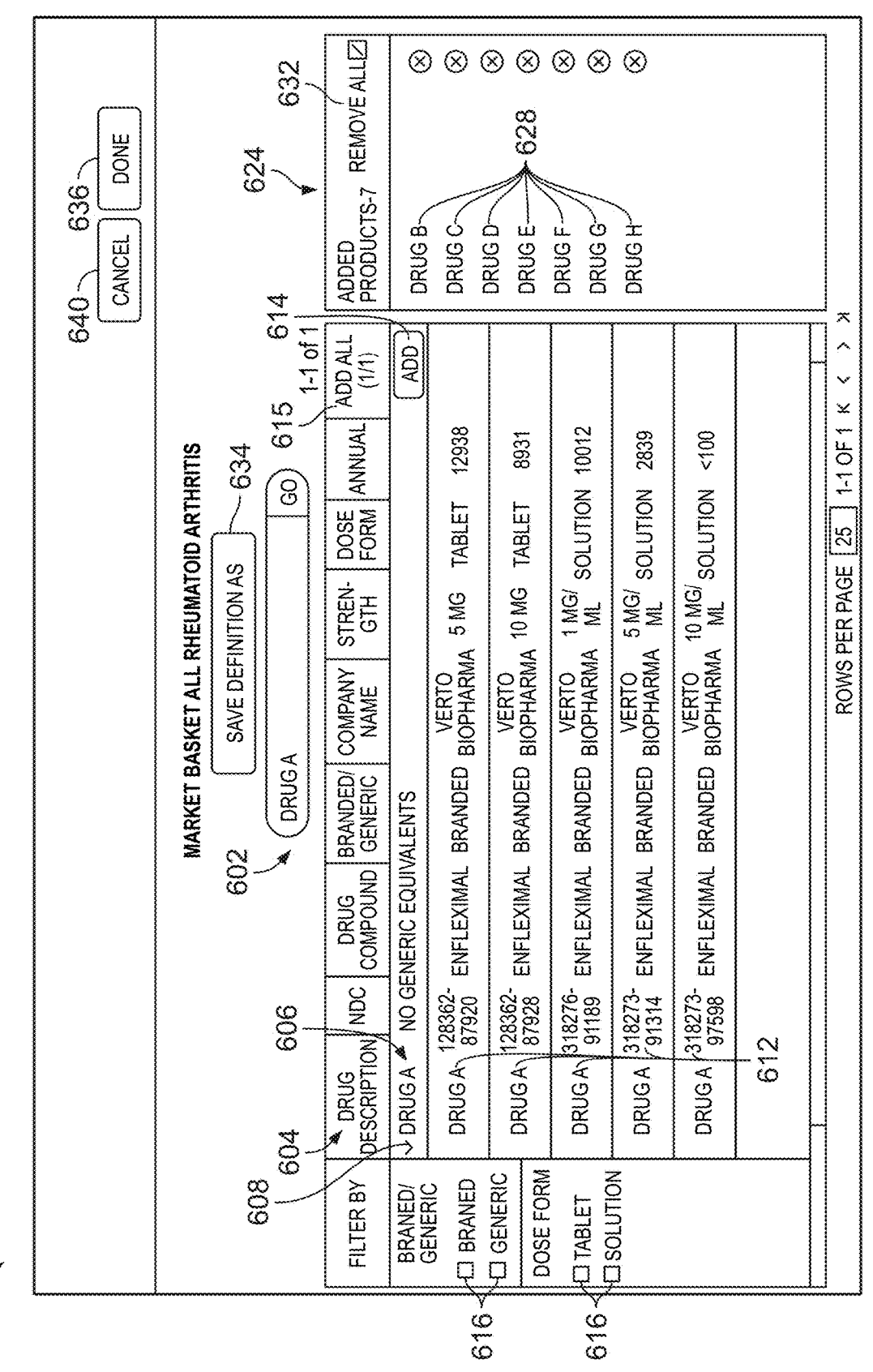
FIG. 6 is an illustration of some aspects of a user interface generated by the query generation and health data analyzation system of FIG. 1 to receive a grouping of medical products, according to an example embodiment.

Referring now to FIG. 6, a medical product group selection page 600 is shown. The medical product group selection page 600 can be displayed on a display of the I/O circuit 180 of the client computing device 112 and, in general, provides the user with an interface (e.g., a page including options, information, and other features that will be described herein) to define a medical product group. For example, through interaction with the medical product group selection page

600 the user of the client computing device 112 can generate or define a medical product group which can then be included in a configuration property and included in the query, which is provided to the provider computing system 104. To access or be navigated to the medical product group selection page 600, the user of the client computing device 112 select or click the search button 406 or the template button 408 of the query page 400.

As shown, the medical product group selection page 600 includes a medical product search bar 602, a medical product search results section 604, multiple search result filter options 616, a medical product group summary section 624, a save new medical group button 634 button, a done/submit button 636, and a cancel button 640. When the user is directed to the medical product group selection page 600, the user is typically trying to edit or create a new medical product group with one or more medical products. As a result, the medical product search bar 602 is a selectable bar with a text entry field and a search or go button. In use, the user of the client computing device 112 may type or enter a medical product identifier (e.g., name, national drug code (NDC), chemical formula) into the text entry field of the medical product search bar 602 and select the go button. When the go button is selected, the client computing device 112 may send a medical product query or request including the medical product identifier to the provider computing system 104. In response, the provider computing system 104 may query or search the medical product repository (not shown) for information pertaining to the medical product identifier. If a result or multiple results are found, the provider computing system 104 may provide the results to the client computing device 112.

In this regard, the medical product search results section 604 is a section of the medical product group selection page 600 in which medical product search results received from the provider computing system 104 are displayed by the client computing device 112. Through interaction with the medical product search results section 604, the user of the client computing device 112 can review and add one or more of the medical product search results to the medical product group. As shown, the medical product search results section 604 includes one or more medical product 606 search results (depending on the search results received from the provider computing system 104) and an add all button 615. The medical product search result 606 is shown to include a toggleable button 608, medical product information 612, and an add button 614.

The toggleable button 608 is a selectable button that hides or displays the medical product information of the respective medical product search result 606. In this regard, the user may select the toggleable button 608 to hide the medical product information 612 and to review the medical product search results 606 more quickly and then select the toggleable button 608 again to see the medical product information pertaining to the respective medical product search result 606 and do a more thorough review.

The medical product information 612 of the medical product search result 606 may be any medical product information described herein but is shown to include a medical product description or brand name, a medical product NDC, a chemical compound of the medical product, a company name, the strength of the medical product, the dose form of the medical product, and the annual count (number sold) of the medical product. As shown, each medical product search result 606 may comprise each type of the respective medical product (e.g., tablet version, solution version, different dosages, etc.) such that only one medical product search result 606 is returned for all forms of a single medical product.

Once the user has reviewed the medical product information 612 of the medical product search result 606 and determines they want to add the medical product to the medical product group, the user may select the add button 614. The add button 614 may add the medical product associated with the medical product search result 606 to the medical product group such that it appears in the medical product group summary 624. Similarly, the add all button 615 may add the respective medical product associated with each search medical product search result 606 of the medical product search results section 604 to the medical product group such that each medical product appears in the medical product group summary6.

Still referring to FIG. 6, the filter options 616 are selectable options or checkboxes that, when selected, filter the medical product search results 606 of the medical product search results section 604. For example, the filter options 616 are shown to include a branded filter option 616, a generic filter option 616, a tablet filter option 616, and a solution filter option 616. If the user of the client computing device 112 were to select the tablet filter option 616, the client computing device 112 may filter the medical product search results 606 and display only medical product search results 606 that are available as a tablet form (e.g., that include medical product information 612 indicating a tablet dose form) in the medical product search results section 604. Likewise, if the user were to select the branded filter option 616, the client computing device 112 may filter the medical product search results 606 and display only medical product search results 606 that are available as a branded medical product (e.g., that include medical product information 612 indicating a branded type of the medical product).

If at any time the user would like to review the medical products added to or currently included in the medical product group, the user can do so using the medical product group summary section 624. The medical product group summary section 624 is a section of the medical product group selection page 600 that provides a summary of the medical products currently included in the medical product group. As shown, the medical product group summary section 624 includes multiple medical product titles or names 628 and a remove all button 632. The medical product names 628 provide a quick idea of which medical products are in the medical product group and each include a remove button. The remove button (i.e., the "X" button on the righthand side of each medical product name 628) is a selectable button that, when selected, removes the medical product identified by the medical product name 628 from the medical product group. Likewise, the remove all button 632 is a selectable button that, when selected, removes all of the medical products identified by the medical products names 628 from the medical product group.

Once the user has finished adding or removing medical products from the medical product group, the user can save the medical product group, cancel the changes to the medical product, or save the medical product group as a new group entirely. To do so, the user can interact with the save new medical group button 634, the done/submit button 636, or the cancel button 640. The save new medical group button 634 is a selectable button that, when selected generates a popup to name the medical group. Once the user has named the medical group, the client computing device 112 will provide the medical product group including the medical products added by the user to the provider computing system 104. The provider computing system 104 may store the medical product group in association with an account of the user in the medical product repository (not shown). The medical product group may then be used as a configuration property and included in the query. Likewise, the done/submit button 636 is a selectable button 636 that, when selected, updates the currently access medical product group to include the medical products specified by the user and provides the updated medical product group including the medical products to the provider computing system 104 for storage as described herein. Lastly, the cancel button 640 is a selectable button that, when selected, discards any changes to the medical product group and returns the user to the query page 300 (i.e., cancels the changes to the medical product group).

Referring now to FIGS. 7A-7D, a query page 700 (also referred to as the second query page 700), which can be displayed on a display of the I/O circuit 180 of the client computing device 112 is shown. In general, the query page 700 provides the respective client computing device 112 with an interface to design and manage the query for projected data records (e.g., the query in the method 200 and the method 300) and provide the query to the provider computing system 104 for execution. For example, via the query page 700, the user may provide the query including one or more requested configuration properties to the computing device 112, which may provide the initial query to the provider computing system 104 for execution therein. In this regard, the provider computing system 104 may provide medical product data, diagnosis data, procedure data, and the like to the respective client computing device 112 to enable display of the query page 700 on the display of the I/O circuit 180. In some embodiments, the first query 700 may be associated with the granularity type of Location-USA.

As shown, the query page 700 includes a medical product display section 710 (also referred to as a first section 710) and an analytic display section 752 (also referred to as a second section). To switch between display of the first section 710 and the second section 752, the query page 700 further includes a first section button 704 and a second section button 750. For instance, in response to a selection of the first section button 704, the query page 700 may display the first section 710 where medical products can be reviewed and selected. In comparison, in response to a selection of the second section button 752, the query page 700 may display the second section 752 where the medical products can be compared via multiple graphs and charts.

Additionally, the second query page 700 includes a save button 705, an undo button 706, a repeat button 707, a download button 708, and a send data button 709. The save button 705 may be a selectable button that, when selected, provides the data (e.g., the query) of the second query page 700 (e.g., the selected medical products) to the provider computing system 104 for storage therein. Then, in response to a request for the data of the second query page 700, the provider computing system 104 may provide the data to the client computing device 112 for display on the second query page 700. The undo button 706 and the repeat button 707 may each be selectable buttons to undo or redo actions on the query page 700 (e.g., unselect a medical product, reselect a medical product, etc.).

The download data button 708 may be a selectable button that, when selected, causes the provider computing system 104 to generate an electronic file (e.g., an Excel file, a CVS file, etc.) including the data of the medical product table 722 to the client computing device 112. Likewise, the send data button 709 may be a selectable button that, when selected, sends the data (e.g., the query) of the query page 700 the provider computing system 104 for validation and execution thereon. In some embodiments, in response to a selection of the send data button 709, the client computing device 112 is navigated to the delivery page 500.

Figure 7A:
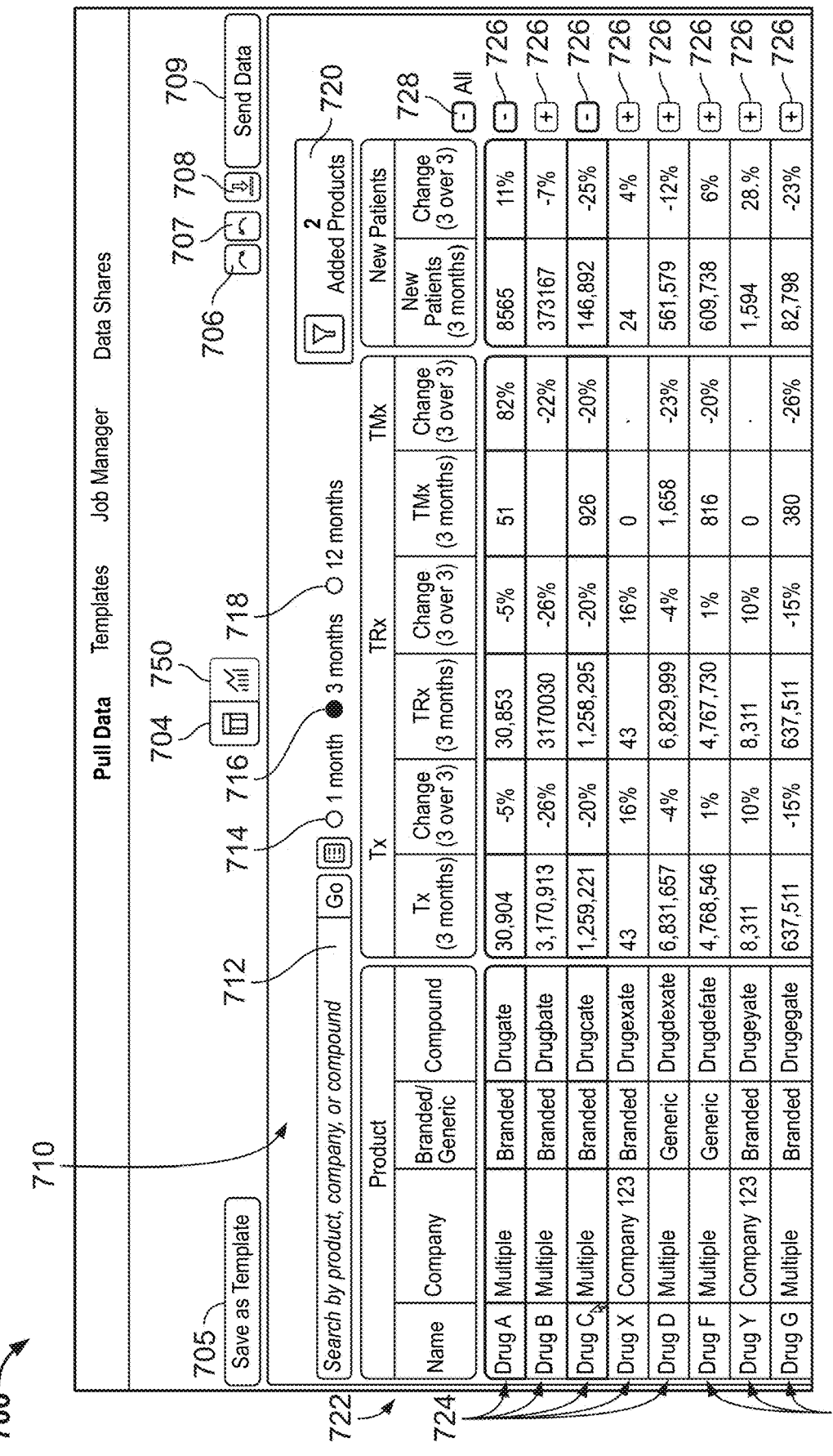
FIGS. 7A-7D are illustrations of some aspects of a user interface generated by the query generation and health data analyzation system of FIG. 1 to receive a query, according to an example embodiment.
Figure 7B:
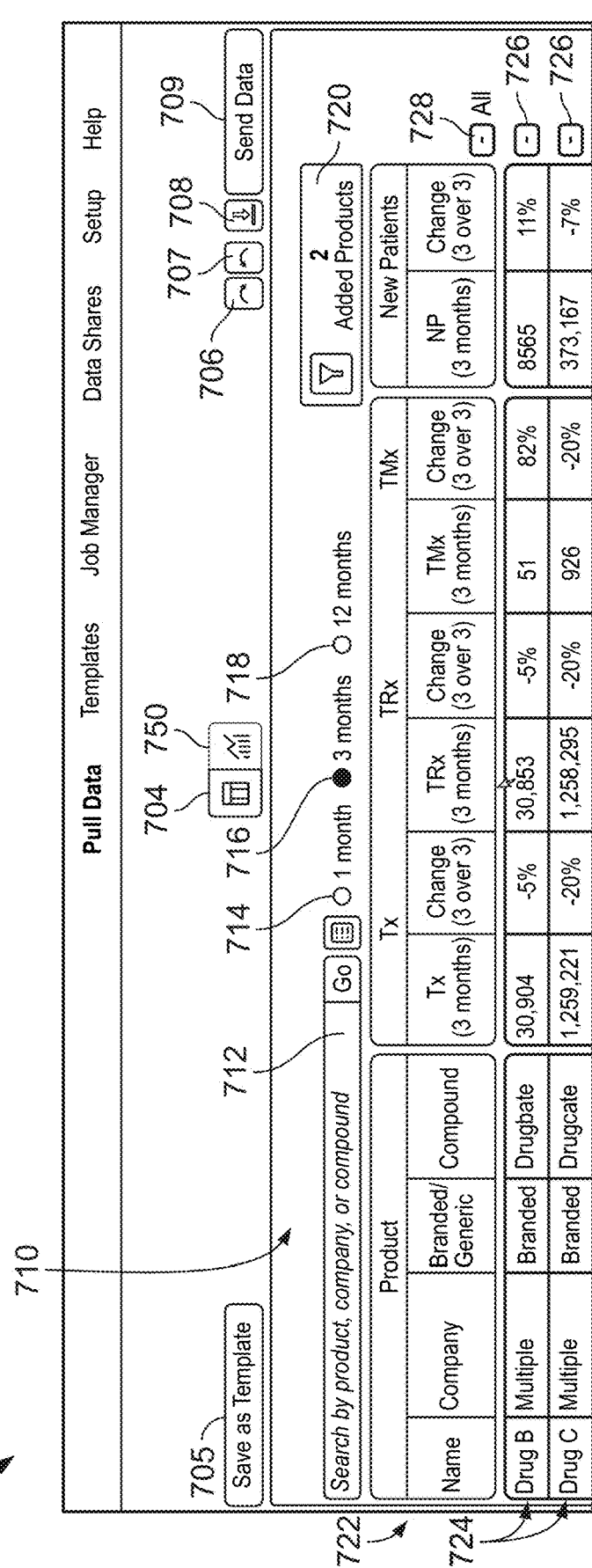

Referring to FIGS. 7A-7B, the first section 710 is an interactive section of the second query page 700 through which the user of the client computing device 112 can select and discard medical products to be included in the generated query. As shown, the first section 710 includes a search field 712, multiple timeframe options (including a first timeframe option 714, a second timeframe option 716, and a third timeframe option 718), an added product filter button 720, and a medical product table 722.

The medical product table 722 may include multiple medical product representations 724 or line listings as well as an add all/remove all checkbox 728. For instance, as shown, the medical product table includes a first medical product representation 724 (e.g., Drug A), a second medical product representation 724 (e.g., Drug B), and so on. Each medical product representation 724 may include projected health data. For instance, each medical product representation 724 is shown to include a product name, a company name, a branded/generic field, a compound or substance field, a total prescription value, a total prescription change percentage, a total number of prescription claims (TRx), an Rx change percentage, a total number of medical claims (TMx), an Mx change percentage, a number of new patients, a new patient change percentage, and an add/remove checkbox 726.

Still referring to FIGS. 7A-7B, the search field 712, the multiple timeframe options, and the added product filter button 720 may each modify the medical product table. For instance, each add/remove checkbox 726 is a checkbox that alternates, when selected, between an add checkbox and a remove checkbox. In this regard, when the query page 700 is first loaded, each add/remove checkbox 726 may be set as removed (such that no medical product representation 724 is selected). Then, in response to a selection of the add/remove checkbox 726, the user of the client computing device 112 may add multiple medical products to filter the medical product table 722 on. Then, in response to a selection of the added product filter button 720, the query page 700 may remove the unselected medical product representations 724 (see FIG. 7B) from the medical product table 722 such that only the selected medical product representations 724 are included in the medical product table 722.

Similarly, the search field 712 may be a selectable and editable search field through which the user of the client computing device 112 can enter and search for a specific medical product (e.g., "Drug X"). In response to a search of a specific medical product via the search field 712, the medical product table 722 may only display medical product representations 724 which match the search criteria results (e.g., a medical product representation 724 associated with Drug X).

Moreover, each of the multiple timeframe options may be a selectable option that, when selected, modifies the timeframe for the values included in the medical product table 722. For instance, in response to a selection of the "3 months" timeframe option 716, each value of the medical product representations 724 (e.g., Tx, TMx, TRx, Tx change %, etc.) is for the specific timeframe selection of 3 months (e.g., Total projected number of prescriptions for the last 3 months, total projected number of prescription claims (Rx) for the last 3 months, total projected number of medical claims (Mx) for the last 3 months, etc.). In some embodiments, the second query page 700 includes other timeframe options (e.g., a 2-year timeframe option, a 3-year timeframe option, a 180-day timeframe option, a 6-month timeframe option, etc.).

Figure 7C:
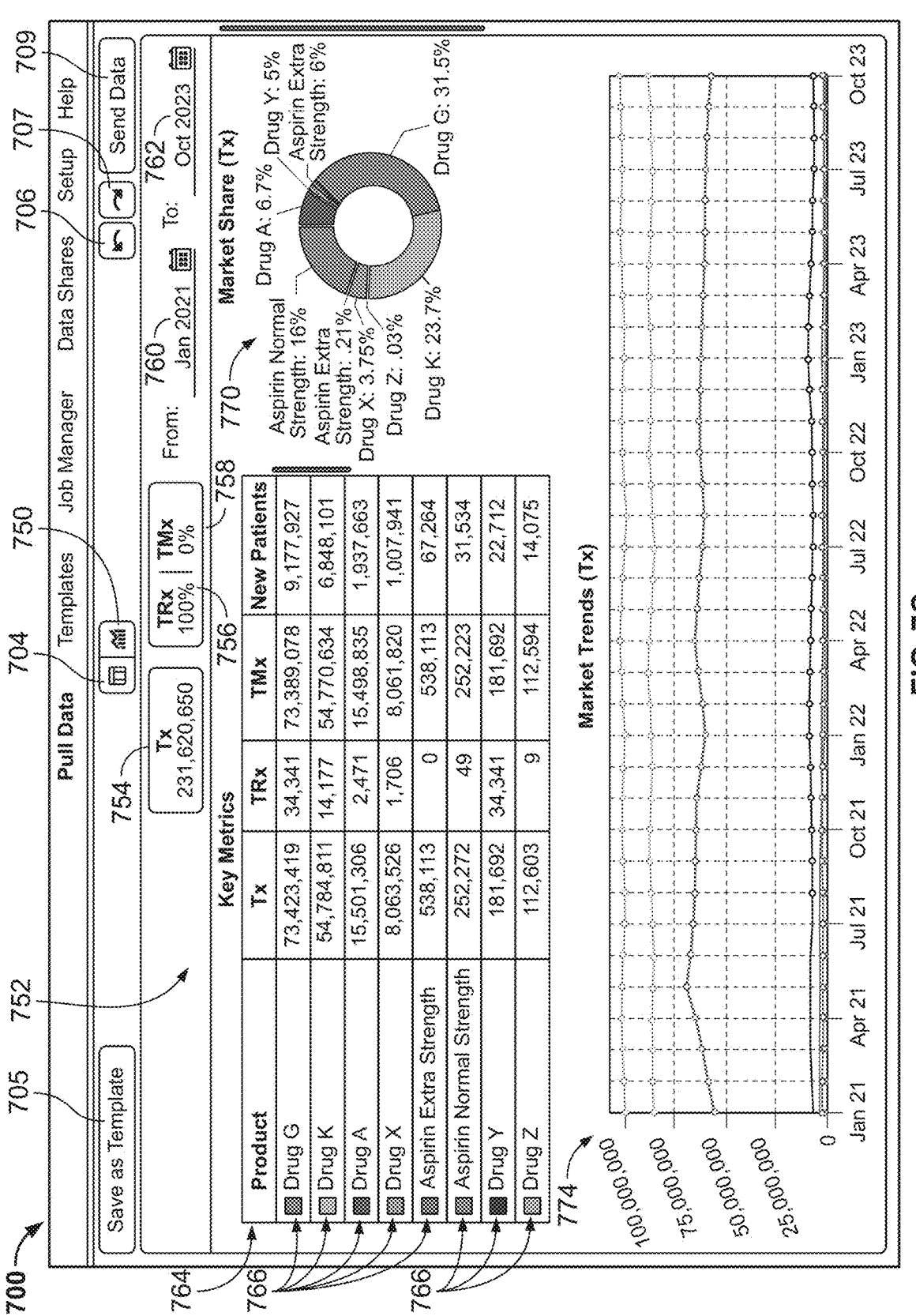
Figure 7D:
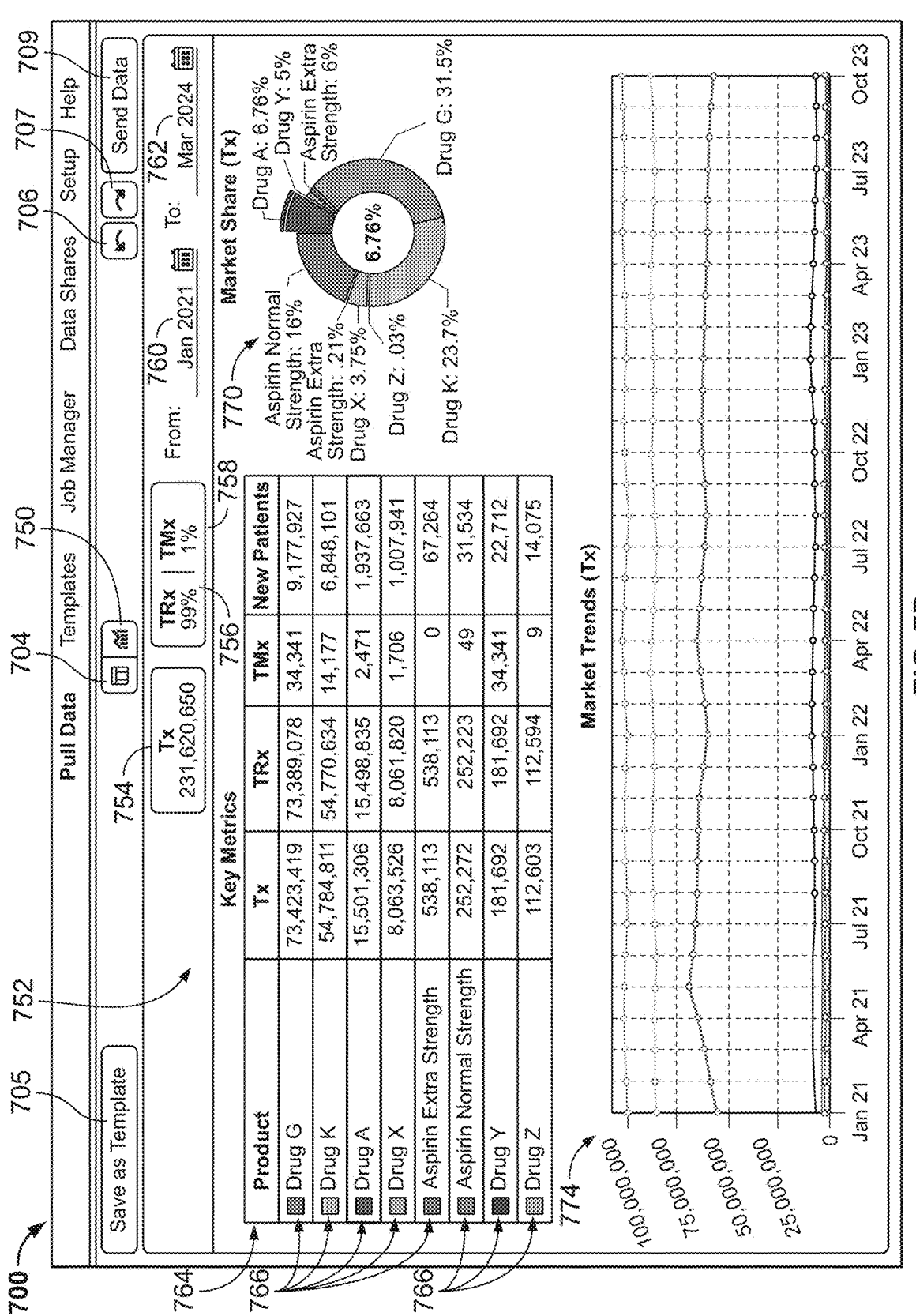

Referring now to FIGS. 7C-7D, the second section 752 is an interactive section of the second query page 700 through which the user of the client computing device 112 can review and analyze the medical products selected via the first section 710. As shown, the second section 752 includes a Tx field 754, a TRx percentage field 756, a TMx percentage field 758, multiple date fields including a start date field 760 and an end date field 762, a medical product table 764, the first chart 770, and the second chart 774.

The Tx field 754 includes and displays the sum of the total prescription values for each of the medical products selected on the first section 710. For instance, as shown in FIG. 7C, the client computing device 112 has selected 8 medical products. Accordingly, the provider computing system 104 may sum the total prescription values for each of the eight medical products and display the summed total prescription value in the Tx field 754.

The TRx percentage field 756 includes and displays the Rx percentage, which compares the total volume of Rx prescriptions to the total volume of prescriptions. For example, the summed total prescription value may be composed of 100 Rx prescriptions and 300 Mx prescriptions (for a total value of 4). Accordingly, the Rx percentage may be 25%, which may be displayed in the TRx percentage field 756. Similarly, the TMx percentage field 758 includes and displays the Mx percentage, which compares the total volume of Mx prescriptions to the total volume of prescriptions. For example, the summed total prescription value may be composed of 100 Rx prescriptions and 300 Mx prescriptions (for a total value of 400). Accordingly, the Mx percentage may be 75%, which may be displayed in the TMx percentage field 758.

The multiple date fields may be utilized to modify the timeframe of the query as well as tune the values of the second section 752 (e.g., the Tx field 754, the TRx percentage field 756, the TMx percentage field 768, the medical product table 764, the first chart 770, and the second chart 774). For instance, the data of the second section 752 may be retrieved and correspond to the multiple date fields. In one specific example, the x-axis of the chart 774 may begin at the start date of the start date field 760 and end at the end date of the end date field 762. In this regard, each of the values displayed on the second section 752 may correspond and be for the dates selected in the multiple fields.

The medical product table 764 may be similar to the medical product table 722 of the first section 710, but provide a condensed version which does not provide for removal or addition of medical products. For instance, the medical product table 764 includes multiple medical product representations 766, similar to the medical products representations 724. Each medical product representation 766 may include projected data records. For instance, each medical product representation 66 is shown to include a total prescription value (Tx), a total number of prescription claims (TRx), a total number of medical claims (TMx), and a number of new patients. Further, each medical product representation 766 may be selectable. For instance, in response to a selection of a medical product representation 766, the second section 752 may highlight or emphasize the data associated with the medical product of the medical product representation 766. FIG. 7D shows an example of the data associated with the medical product being highlighted. In response to a selection of the medical product representation 766 for Drug A. For instance, the row including the medical product representation 766 in the medical product table 764 may be highlighted with a specific color. In another example, the chart 770 may popout the portion or slice of the pie chart associated with the medical product as well as include the percentage of the medical product in the middle thereof. In another example, the line of the chart 774 associated with the medical product may be bolded or highlighted.

The charts 770 and 774 are each interactive charts that may be generated based on the statistical values described herein. For example, as shown, the chart 770 is a pie chart that is generated based on the selected medical products (e.g., selected via the medical product table 722) and the market share percentage associated with each medical product. For instance, the chart 770 includes a first portion or slice for the first selected medical product (e.g., Drug A) with an associated market share percentage (6.7%), a second portion or slice for the second selected medical product (e.g., Drug K) with an associated market share percentage (23.7%), and so on.

Likewise, the chart 774 is a line chart that is generated based on the sets of projected data records, for each selected medical product, and the axis tick marks described herein. For instance, the chart 774 includes a first graphed line for the projected data records of the first medical product, a second graphed line for the projected data records of the second medical product, and so on. Further, the chart 774 includes multiple y-axis tick marks and x-axis tick marks.

Figure 8A:
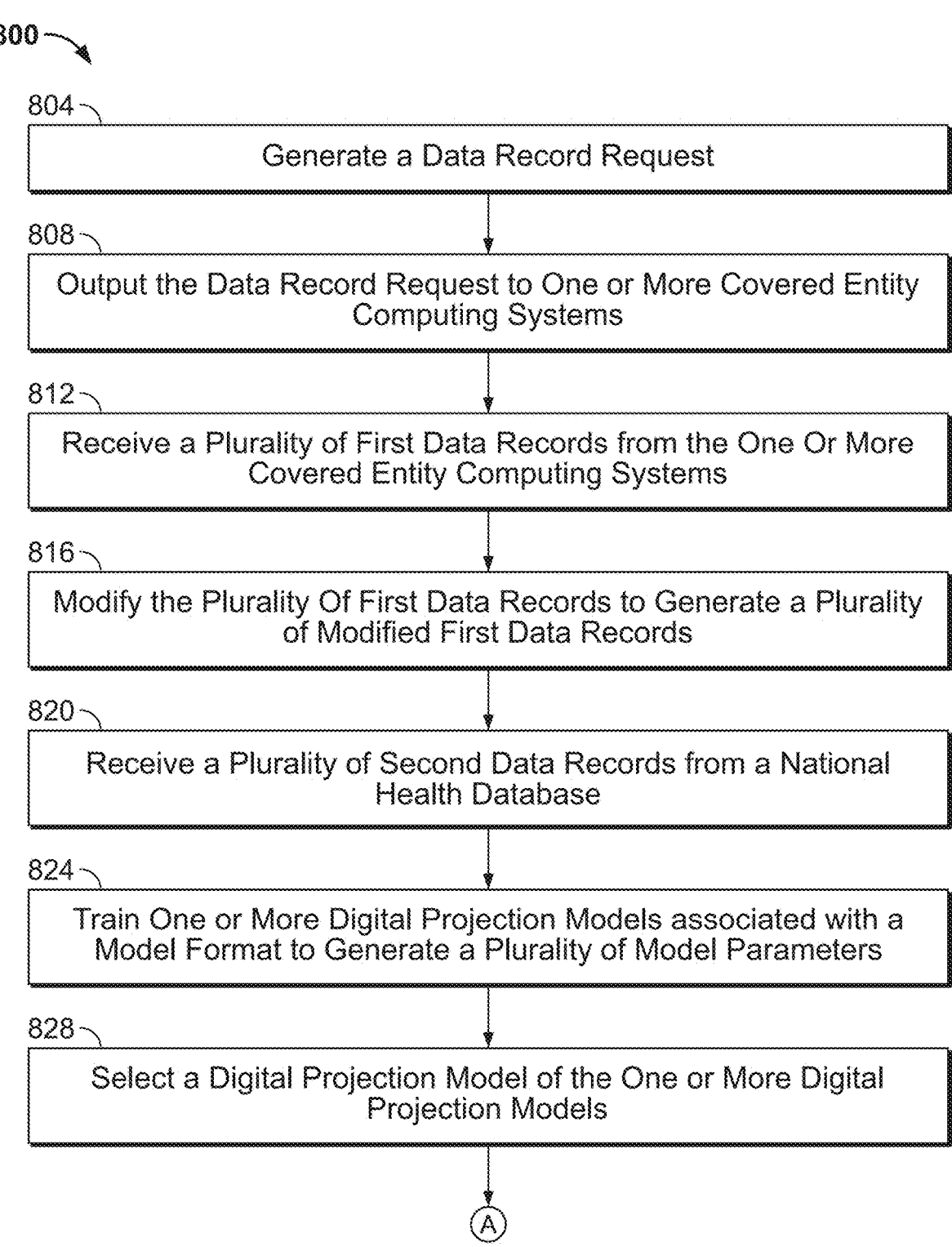
FIGS. 8A-8C are a flow diagram of a method for generating a new set of projected data records and querying the new set of projected data records from a repository, according to an example embodiment.
Figure 8B:
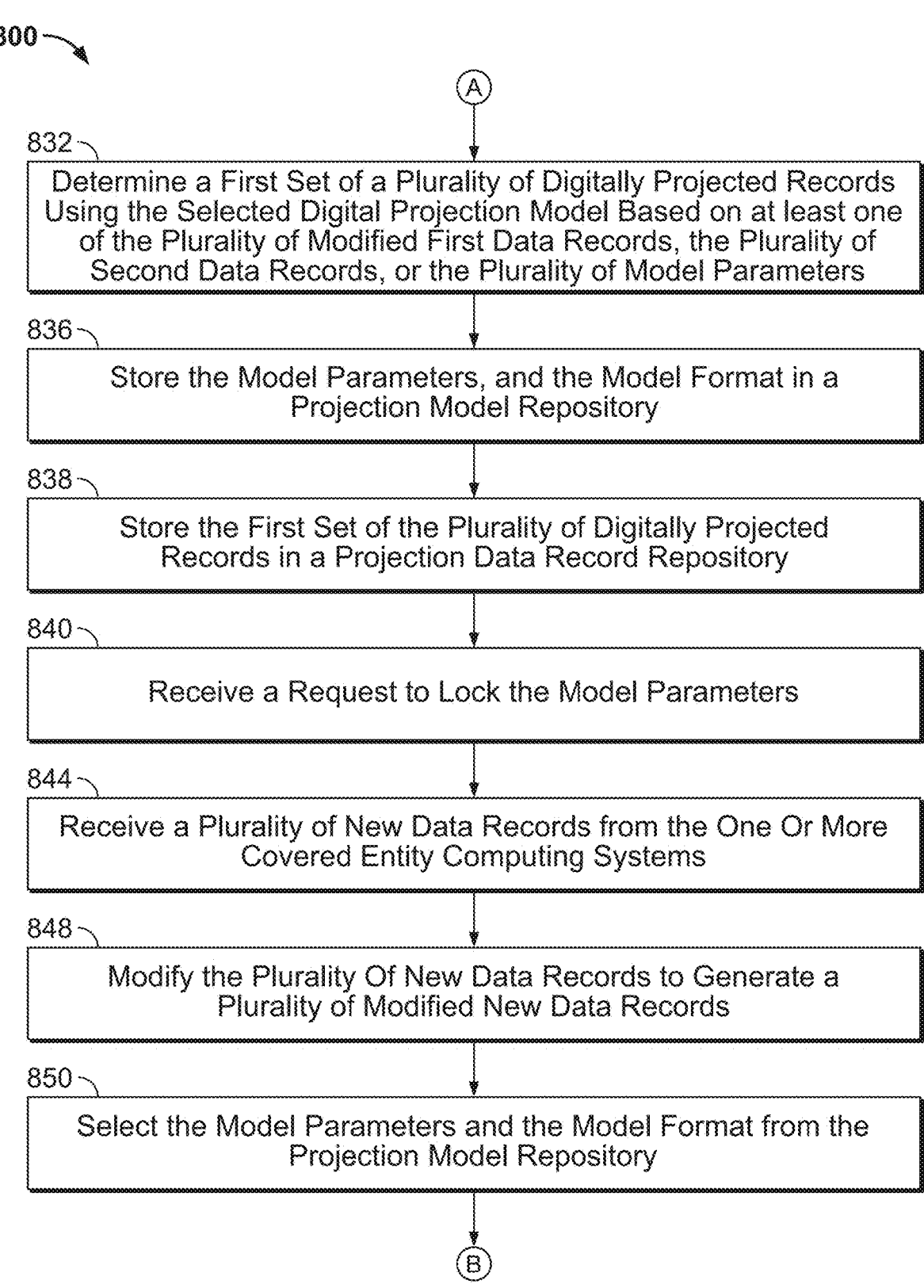
Figure 8C:
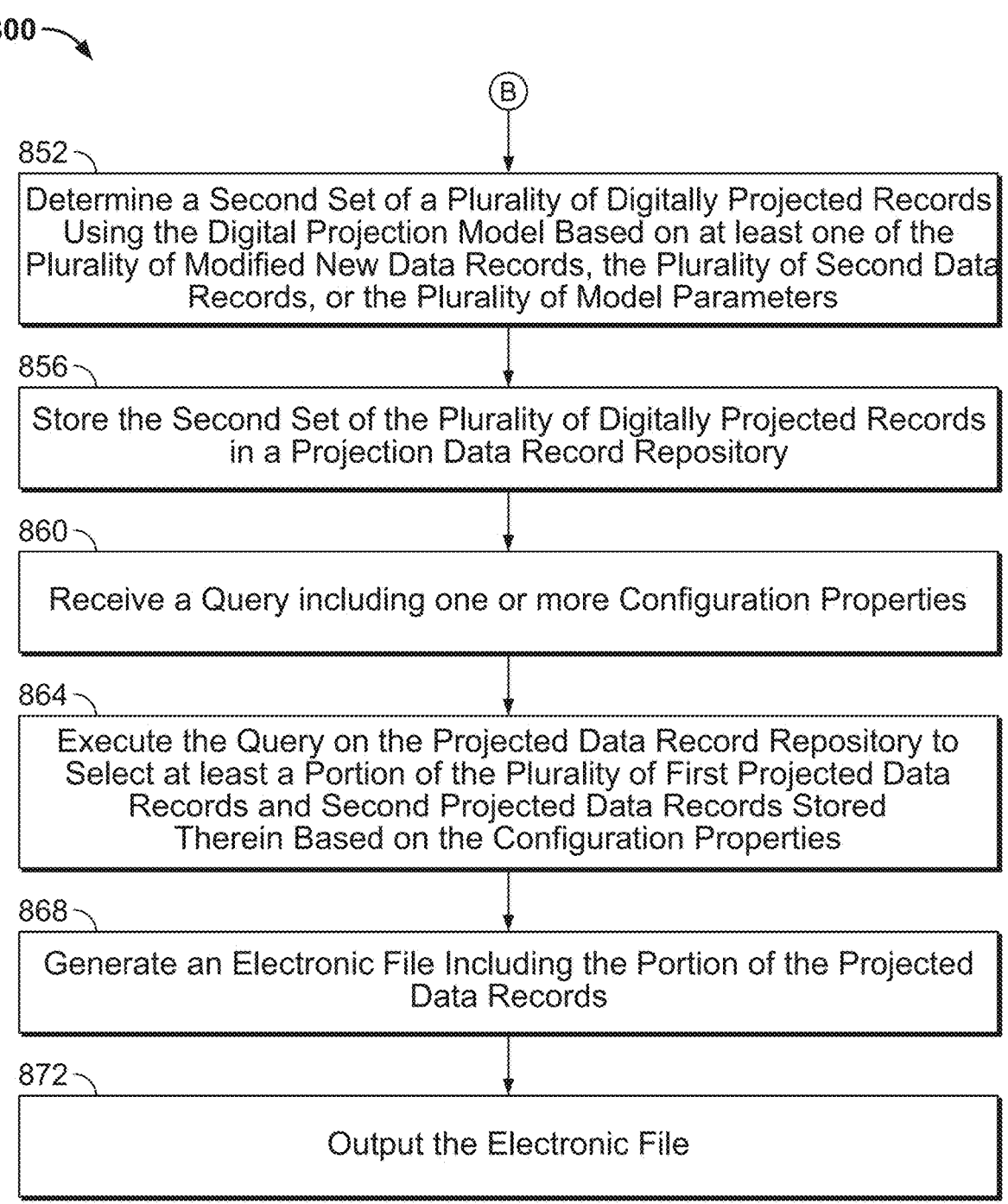

Referring now to FIGS. 8A-8C, a method 800 for generating a second or new set of projected data records and querying the new set projected data records is shown, according to an example embodiment. Method 800 commences at step 804 at which the provider computing system 104 generates a data record request. Step 804 may be the same as step 204 of the method 200. As described herein, the data record request may be generated and populated with various types of data such as HCP data, consumer data, medical product data, and a timeframe. In some embodiments, the provider computing system 104 may receive or retrieve each various type of data (e.g., retrieve HCP data from an HCP repository (not shown), retrieve consumer data, etc.) prior to step 204. The data record request may request data records (e.g., health data records, Rx records, Mx records, etc.) that are associated with or matches the data included in the data record request.

Once the provider computing system 104 has generated the data record request, the method 800 proceeds to step 808 at which the provider computing system 104 provides the data record request to the one or more covered entity computing systems 108. In some embodiments, the provider computing system 104 may provide the data record request over the network 118 via the network interface 126 to the one or more covered entity computing systems 108.

Once the provider computing system 104 has provided the data record request to the one or more covered entity computing systems, the method 800 proceeds to step 812 at which health data records (also referred to as first data records) are received from the one or more covered entity computing systems 108. Step 812 may be the same as the step 212 of the method 200. The first data records may be received in response to the provider computing system 104 providing the data record request to the one or more covered entity computing systems 108 and may be or include Rx records, Mx records, and other data records described herein. For example, the first data records may be prescription claims (Rx) data records that include deidentified PHI or PII, medical product data, diagnosis data (e.g., a diagnosis code), HCP data (e.g., an NPI of a prescribing HCP), date/time data, facility or health care system location data, and transaction data. In another example, the first data records may be medical claims (Mx) data records that includes deidentified PHI or PII, medical product data, procedure data (e.g., procedure code), diagnosis data (e.g., a diagnosis code), HCP data (e.g., an NPI of a prescribing HCP), date/time data, facility or health care system location data, and transaction data.

As described herein, the PHI or PII of the first data records may be deidentified, by the one or more covered entity computing systems 108, in a variety of ways including through encryption, tokenization, and use of a hash function. In some embodiments, the one or more covered entity computing systems (e.g., the covered entity computing system 108) may use a consistent form of deidentification such that the same PHI or PII input will return the same hash value or token. For example, if a data record included the name "John Smith," a resulting deidentified hash value may be "1234321." To be consistent, each of the one or more covered entity computing systems, when identifying the name "John Smith," may then return the hash value "123431." By using the same hash function across the one or more covered entity computing systems, the provider computing system 104 can make additional connections between the received data records and generate HCP insights and metric values. Further, less processing power is required by the provider computing system 104 as most of the data record matching is completed by the one or more covered entity computing systems prior to the data records being received by the provider computing system 104.

Once the provider computing system 104 has received the first data records, the method 800 proceeds to step 816 at which the provider computing system 104 modifies each first data record. Step 816 may be the same as the step 216 of the method 200. For instance, the provider computing system 104 may further modify each data record to enhance or augment (i.e., add data to) the data record. In one example, the provider computing system 104 may determine the data record includes a diagnosis code and/or name. Accordingly, the provider computing system 104 may match the diagnosis code with a diagnosis code repository (not shown) and return a first (primary) diagnosis code class and a second diagnosis code class associated with the diagnosis code. The provider computing system 104 may then add the primary diagnosis code class and the second diagnosis code class to the data record.

In another example, the provider computing system 104 may determine the data record includes a zip3 code, but not a state. Accordingly, the provider computing system 104 may determine a state associated with the zip3 code and add the state to the data record. In another example, the provider computing system 104 may modify the data records to remove data records that are empty (e.g., include null values, are not fully populated, etc.). In another example, the provider computing system may determine that the data records includes an HCP NPI code for a prescribing HCP. Accordingly, the provider computing system 104 may match the HCP NPI with an HCP repository (not shown) and populate the data record with various portions of HCP data (e.g., HCP name, HCP zip code, HCP specialty (e.g., Pediatrician, Cardiologist, etc.), etc.).

In some embodiments, after receiving and/or modifying the first data records, the provider computing system 104 may store the modified first data records in the master data record repository 130. In some embodiments, the provider computing system 104 may add the modified first data records to the master data record repository 130 to replace the previously stored set of data records.

Once the provider computing system 104 has modified the first data records, the method 800 proceeds to step 820 at which the provider computing systems 104 receives or selects second data records (also referred to as government data records) from the one or more national health repositories 120. The second data records may include medical product information (e.g., NDCs), location information (e.g., zip code for a specific Rx or Mx, state for a specific Rx or Mx, country for a specific Rx or Mx, etc.), deidentified PHI or PII, and/or a timeframe (e.g., Jan. 1, 2022-Jan. 2, 2022) associated with the second data records. In some embodiments, the government data records identifies whether a data record is Rx or Mx information. In other embodiments, the provider computing system 104 receives a first set of government data records that are each a RX record and a second set of government data records that are each an Mx record.

Once the provider computing system 104 has received the second data records, the method 800 proceeds to step 824 at which the provider computing system 104 trains or parameterizes one or more digital projection models based on data records (e.g., the modified first data records or the second data records) and/or the feature data set to generate one or more model parameters. The feature data set may include the first data records, the second data records, the HCP data, the consumer data, location data (e.g., of the HCP data) and/or other data described herein. In some embodiments, the provider computing system 104 may aggregate the first data records, the second data records, the HCP data, the consumer data, location data (e.g., of the HCP data) and/or other data described herein such that each is only included as a count/sum or aggregated value in the feature data set. For instance, the provider computing system 104 may aggregate the first data records such that seven separate first data records associated with a specific provider or NPI and medical product are transformed into the number 7. This process may be repeated for each of the data records such that the feature data set includes multiple data counts/sums or aggregated values.

For instance, at step 824, the provider computing system 104 may train or parameterize each digital projection model (e.g., the first digital projection model, the second digital projection model, the third digital projection model, and so on). Likewise, each digital projection model may be associated with a specific model format or data schema.

For instance, the first digital projection model may be associated with a specific version (e.g., version 2.0) of the first digital projection model data schema. The data schema may define the logical organization of data, the relationships between data elements, and the constraints that ensure data integrity. In this regard, the data schema may define the specific fields, data types, and the format of the data to be used in training the digital projection model (e.g., the data records) and prevent errors from appearing during the loading of the data by the digital projection model. For instance, when determining or generating the digitally projected values (e.g., step 832 or step 852), the provider computing system 104 may verify the digital projection model by comparing the specific version of the first digital projection model data schema to that of the data records.

By utilizing and verifying the digital projection model data schema or model format, the present systems and methods provide a technical improvement to model performance, reliability, and maintainability, as well as enhanced model robustness and stability. For instance, because the digital projection models are trained on a specific data format, including data types, column names, and value ranges, the specific format of the data schema provides for data integrity. For instance, if the data schema or model is new, unseen data changes, degrade the model's performance or it might fail entirely. For example, a model expecting a numerical feature might fail if it receives a categorical one instead. By using data schema versions and verifying the schema of incoming data against the expected version, the present systems provide for improved model stability and runtime performance, thereby requiring less processing power and memory by ensuring the model is utilizing the correct data.

Likewise, because the provider computing system 104 utilizes multiple digital projection models, the model data schema or model format provides for enhanced order and verification. For instance, by verifying the digital projection model based on the model data schema, the present systems and methods ensures that every new batch of data is checked before it's used, which provides for less data incompatibility issues and less errors when running the digital projection model.

To parameterize each digital projection model and generate the one or more parameters of the digital projection model, the provider computing system 104 may fit the digital projection model to the feature data set including the data records (e.g., the first data records and/or the second data records) to define the model's internal, adjustable variables (i.e., parameters) that are learned from data. The parameters are the key internal components that a model generates. They are not set manually but are instead the direct result of the training process.

Once the provider computing system 104 has trained each of the digital projection models, the method 800 proceeds to step 828 at which the provider selects a first digital projection model of the set of trained digital projection models. For instance, the provider computing system 104 may determine the specific digital projection model based on the volumes, quality, and types of data available (e.g., the number and quality of the first data records, the number and quality of the second data records, etc.). For instance, the provider computing system 104 may select the first digital projection model based on the volume of the first data records being large and of high quality, whereas the provider computing system 104 may select the second digital projection model based on the volume of the first data records being low and/or of low quality or the volume of the second data records being high and/or of high quality. In another example, when the volume and/or quality of the first data records is approximately equivalent to that of the third digital projection model, the provider computing system 104 may select the third digital projection model.

In some embodiments, at or before step 828, the provider computing system 104 may determine or receive a volume metric and a quality metric or value associated with the first data records. Likewise, at or before step 828, the provider computing system 104 may determine or receive a volume metric or value and a quality metric or value associated with the second data records.

In some embodiments, the provider computing system 104 may output a file including the digital projection models, quality and volume data associated with the data records, and a text query to an artificial intelligence (AI) computing system (not shown). The file may further include an application programming interface (API) key. Then, in response, the provider computing system 104 may receive a response file from the AI computing system, which may indicate the digital projection model to be selected/determined at step 828.

Once the provider computing system 104 has selected the digital projection model, the method 800 proceeds to step 832 at which the provider computing system 104 generates a first set of projected data records based on at least one of the modified first data records, the second data records, and/or the model parameters using the selected projection model. As described herein, the digital projection models are models (e.g., machine-learning (ML) models, statistical models, etc.) used to determine digitally projected data records (i.e., total projected prescription counts) based on the known values (e.g., the first data records, the second data records, etc.). Each set of projected data records may include multiple digitally projected values that are each associated with a different specific location. In some embodiments, the provider computing system 104 may generate multiple sets of projected data records at step 832.

In some embodiments, each set of projected data records may include multiple digitally projected values that are each associated with a specific prescriber or HCO (e.g., HCP). For instance, a set of projected data records may include a first digitally projected value that is associated with (i.e., projected specifically for) a first HCP or HCO (as identified by NPI), a second projected value that is associated with (i.e., projected specifically for) the first HCP or HCO, and so on. In this regard, each digitally projected value of the set of digitally projected records is associated with the correlated NPI.

In some embodiments, each set of projected data records may be associated with a specific medical product and a location or country (e.g., the USA). Then, each digitally projected value of the set of projected data records may be associated with a specific timeframe. For instance, a set of projected data records may include a first digitally projected value that is associated with (i.e., projected specifically for) a first country (e.g., the USA), a first medical product (e.g., drug X), and a first timeframe (e.g., May 2021); a second projected value that is associated with (i.e., projected specifically for) the first country, the first medical product, and a second timeframe (e.g., June 2021); and so on In some embodiments, the provider computing system 104 may determine a set of projected data records for multiple dates/times (e.g., day, month, year, week), for each medical product, and for each data record type (e.g., Mx or Rx). For instance, the provider computing system 104 may determine a first set projected data records for a first month, a first data record type, and a first medical product; a second set of projected data records for a second month, a second data record type and the first medical product; a third set of projected data records for a second month, the first data record type, and a second medical product; and so on. In some embodiments, the provider computing system 104 may generate a first set of projected data records based on the second data records using the selected digital projection model and a second set of projected data records based on the second data records and the modified first data records using the digital projection model.

Each projected data record (e.g., each digitally projected value) may be or include a projected number of prescriptions (e.g., Rx or Mx transactions) for a specific date/time or timeframe, a specific medical product, a specific NPI or location, and/a specific data record type (e.g., Mx (in-office dispensed prescriptions claims) or Rx (pharmacy-dispensed prescription claims)). For example, because the one or more covered entity computing systems 112 do not cover or include data records associated with all possible prescriptions, the provider computing system 104 must project the missing portions of the data records. For instance, the covered entity computing systems 112 may include data records associated with 40% of all prescriptions in the United States. As a result, using the digital projection models, the provider computing system 104 may project the remaining 60% of prescriptions by determining the projected data records, as described further herein.

In some embodiments, the provider computing system 104 may generate a set of projected data records and use the set of projected data records to determine another, summed, set of projected data records. For example, the provider computing system 104 may determine a set of projected data records that is associated with a specific medical product, a specific timeframe (e.g., the month of May 2021), a specification location (e.g., the zip code 53032), and a specific data record type (e.g., Rx). In this regard, each projected data record may be associated with a specific day of the month of May 2021 (e.g., a first digitally projected value associated with May 1, 2021; a second digitally projected value associated with May 2, 2021; and so on). Then, to determine a summed projected data record for May 2021, the provider computing system 104 may sum the set of projected data records by adding each digitally projected value.

In another example, the provider computing system 104 may generate a first set of projected data records (e.g., with a data record type of Rx) and a second set of projected data records (e.g., with a data record type of Mx). Then, for matching HCPs (e.g., based on NPI), the provider computing system 104 may combine or sum one or more of the digitally projected values of the first set of projected data records and the second set of projected data records to generate a third set of projected data records. In this regard, the Mx values and Rx values may be projected separately but combined to generate total prescription counts for HCPs and medical products.

In another example, the provider computing system 104 may combine or add one or more pieces of the projected data records to generate a second set of digitally projected data records, as described with regard to the methods 200 and 300. In some embodiments, at or after step 832, the provider computing system 104 may determine multiple sets of projected data records using one or more of the digital projection models within the projection model repository 134. For instance, the projection model repository 134 may include a first projection model (e.g., a binary classification projection/forecasting model), a second projection model (e.g., a CNN model), and a third projection model (e.g., a linear regression model). As a result, the provider computing system 104 may determine a first set of projected data records using the first digital projection model, a second set of projected data records using the second digital projection model, and a third set of projected data records using the third digital projection model. Then, the provider computing system 104 may determine a confidence score or value, a lower bound value, and/or a higher bound value for each set of projected data records. Then, the provider computing system 104 may rank each of the sets of projected data records (e.g., based on the respective confidence score, based on a lower bound value, based on a higher bound value) and select one of the sets of projected data records (e.g., the highest confidence score that is above the lower bound value and below the higher bound value, the highest confidence score, etc.).

In this regard, at step 832, the provider computing system 104 may modify the three sets of data records to remove the other sets (e.g., the unselected set of projected data records) to select a final set of data records based on the rank of each set of projected data records. For instance, the provider computing system 104 may determine a first set of projected data records, a second set of projected data records, and a third set of projected data records, using a separate digital projection model for each set. Then, the provider computing system 104 may rank each respective set of projected data records. Then, based on the rankings, the provider computing system 104 may select the final set of projected data records.

Once the provider computing system has generated the first set of digitally projected values, the method 800 proceeds to step 836 at which the provider computing system 104 stores the model parameters and the model format may be stored in the projection model repository 134. In some embodiments, at step 824 (e.g., directly after training each model), the provider computing system 104 may store the model parameters and the model format may be stored in the projection model repository 134. In this regard, at or after step 824, the provider computing system 104 may store the model parameters for each digital projection model (as compared to the model parameters for the digital projection model that generated the final set of digital projection values).

In some embodiments, at or after step 836 and selecting the final set of projected data records, the provider computing system 104 may generate a digital projection model data record associated with the model used to generate the final set of projected data records (e.g., the model that generated the projected data records with the highest confidence score). The digital projection model data record may include the model parameters, the model format, and one or more pieces of metadata. The metadata may include data pertaining to the digital projection model (e.g., date the digital projection model was last used or modified, author, model version, and the like). Then, at step 836, the provider computing system 104 may store the digital projection model data record in the projection model repository 134.

Once the provider computing system 104 the model parameters and the model format in the projection model repository 134, the method 800 proceeds to 838 at which the provider computing system 104 stores the first set of projected data records in the projected data record repositories 132.

Once the provider computing system 104 has stored the first set of projected data records in the projected data record repositories 132, the method 800 proceeds to step 840 at which the provider computing system 104 receives a request to lock or fix the model parameters. In some embodiments, the request may specifically identify the set of digitally projected records (e.g., identify the granularity type and/or the medical product). In other embodiments, the request may identify multiple sets of digitally projected values. In some embodiments, the request may be received from the client computing device 112.

In other embodiments, at step 840 the provider computing system 104 may generate a request or file including the digital projection models, quality and volume data associated with the data records, the first set of digitally projected values, and/or a text query, and output the request or file to an artificial intelligence (AI) computing system (not shown). The file may further include an application programming interface (API) key. Then, in response, the provider computing system 104 may receive a response file from the AI computing system, which may include an indication or request to lock the projection model parameters. In some embodiments, the response file may include an indication or request to unlock the projection model parameters. For instance, the AI computing system may determine the projections have drifted or started to not reflect the actual data sets (e.g., the data records), and generate an indication to unlock the projection model parameters.

Once the provider computing system 104 has received the request to lock the model parameters, the method 800 proceeds to step 844 at which the provider computing system 104 receives multiple new data records. In some embodiments, prior to step 844, the provider computing system 104 may generate a data record request and output the data record request to one or more covered entity computing systems 108. The new data records may be similar or the same as the first data records (e.g., health data records), but be "new" in that they were not available when the provider computing system 104 output out the original data record request (step 808). For instance, at step 812, the provider computing system 104 may receive a first data record for an Mx prescription with a date of Aug. 10, 2024, a second data record for an Rx prescription with a date of Aug. 10, 2024 and a third data record for an Rx prescription with a date of Aug. 11, 2024. However, a fourth data record for an Rx prescription of Aug. 8, 2024 may not have been available (e.g., present in the covered entity computing system 108). Accordingly, at step 844, the provider computing system 104 may receive the new data records including the fourth data record therein.

Once the provider computing system 104 has received the new data records, the method 800 proceeds to step 848 at which the provider computing system 104 modifies the plurality of new data records. For instance, the provider computing system 104 may further modify each new data record to enhance or augment (i.e., add data to) the new data record. In one example, the provider computing system 104 may determine the data record includes a diagnosis code and/or name. Accordingly, the provider computing system 104 may match the diagnosis code with a diagnosis code repository (not shown) and return a first (primary) diagnosis code class and a second diagnosis code class associated with the diagnosis code. The provider computing system 104 may then add the primary diagnosis code class and the second diagnosis code class to the data record.

In another example, the provider computing system 104 may determine the data record includes a zip3 code, but not a state. Accordingly, the provider computing system 104 may determine a state associated with the zip3 code and add the state to the data record. In another example, the provider computing system 104 may modify the data records to remove data records that are empty (e.g., include null values, are not fully populated, etc.). In another example, the provider computing system may determine that the data records includes an HCP NPI code for a prescribing HCP. Accordingly, the provider computing system 104 may match the HCP NPI with an HCP repository (not shown) and populate the data record with various portions of HCP data (e.g., HCP name, HCP zip code, HCP specialty (e.g., Pediatrician, Cardiologist, etc.), etc.).

In some embodiments, after receiving and/or modifying the new data records, the provider computing system 104 may store the modified first data records in the master data record repository 130. In some embodiments, the provider computing system 104 may add the modified new data records to the master data record repository 130 to replace the previously stored set of data records.

In some embodiments, after step 848, the provider computing systems 104 receives or selects second new data records (also referred to as government data records) from the one or more national health repositories 120.

Once the provider computing system 104 has modified the new data records, the method 800 proceeds to step 850 at which the provider computing system 104 selects projection model record including the model parameters and the model format from the projection model repository 134. In some embodiments, at or after step 850, the provider computing system 104 may verify the new modified data records, the second data records, the first data records, and other data records to be used in determining projected data records. For instance, the provider computing system 104 may verify the data records based on the model format of the data records and the model format of the selected projection model. If the model formats match (e.g., the data records are version 2.0 of the model format and the digital projection model record selected has the same version of the model format, the provider computing system 104 may proceed to step 852 of the method 800. In comparison, if the model formats do not match, the method 800 may end.

Once the provider computing system 104 has selects the model parameters and the model format from the projection model repository 134, the method 800 proceeds to step 852 at which the provider computing system 104 determines a second set of projected data records. The second set of projected data records may be determined based on the modified first data records, the second data records, the modified new data records, and/or the model parameters.

The second set of projected data records may be determined similarly to the first set of projected data records. In some embodiments, the first set of digitally projected values may be projected for a first specific timeframe (e.g., a month, a year, etc.), and the second set of digitally projected values may be projected for a second specific timeframe (e.g., a week, a month, etc.) that is shorter than the first specific timeframe.

Once the provider computing system 104 has determined or generated the second set of digitally projected values, the method 800 proceeds to step 856 at which the provider computing system 104 stores the second set of digitally projected values in the projection data record repositories 132.

Once the provider computing system 104 has stored the set of projected data records in the projected data record repositories 132, the method 800 proceeds to step 860 at which the provider computing system 104 receives a query including one or more configuration properties. Step 860 may be similar or the same as step 236 of the method 200. In some embodiments, the query may be received from the client computing device 112. As described herein, the query may be designed by the user via the client computing device 112 and provided to the provider computing system 104 for cleaning and generation. For instance, the provider computing system 104 may generate a query page (also referred to as a query-designer or builder page, such as the first query page 400 or the second query page 700) and provide the query page to the client computing device 112 for rendering and display thereon. Through interaction with the query page, the user of the client computing device 112 may design the query and provide the query to the provider computing system 104. The query may include multiple configuration properties (e.g., a first configuration property, a second configuration property, a third configuration property, etc.) and one or more operators, as will be described further herein. In some embodiments, the query may be received in a file generation request that further includes a specific file type and a file destination address.

Once the provider computing system 104 has received the query from the client computing device 112, the method 800 proceeds to step 864 at which the provider computing system 104 (and more particularly the processing circuit 128) executes the (final) query on the corresponding projected data record repositories 132 to select/retrieve or receive at least a portion of the projected data records stored in the projected data record repository 132. Step 864 may be the same as step 240 of the method 200. For instance, at step 864, the provider computing system 104 may provide the (final) query to the projected data record repository 132 which may then retrieve the matching or resulting projected data records from therein. In another example, the provider computing system 104 (and more particularly the processing circuit 128) may parse the projected data record repository 132 based on the query and select or retrieve the matching or resulting projected data records.

Once the provider computing system 104 has executed the query and selected the portion of the data records from the projected data record repository 132, the method 800 proceeds to step 868 at which the provider computing system 104 generates an electronic file including the selected portion of the projected data records.

After provider computing system 104 has generated the electronic file, the method 800 proceeds to step 872 at which the electronic file is provided or output. In some embodiments, the electronic file is output to the file destination address of the electronic file generation request. The file destination address may be any type of address or destination (e.g., IP address, web address, email address, file transfer protocol (FTP) address, and the like) to which the electronic file may be electronically transmitted or provided. In one example, the file destination address may be another server or circuit of the provider computing system 104 that is configured to receive the electronic file (e.g., Veeva Nitro®). In another example, the file destination address may be a web address of the Amazon S3® cloud storage web service. In another example, the file destination address may be the IP address of the client computing device 112, and the electronic file may be provided to the client computing device 112.

The embodiments described herein have been described with reference to the drawings. The drawings illustrate certain details of specific embodiments that implement the systems, methods, and programs described herein. However, describing the embodiments with drawings should not be construed as imposing on the disclosure any limitations that may be present in the drawings.

It should be understood that no claim element herein is to be construed under the provision of 35U.S.C § 112 (f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit"

may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexors, registers, capacitors, inductors, diodes, wiring, and so on.

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other embodiments, two or more processors may be coupled via a bus to enable independent, parallel, pipelined, or multi-threaded instruction execution. Each processor may be implemented as one or more general purpose processors, application specific integrated circuits (ASICs), field programmable gate arrays (FPGAs), digital signal processors (DSPs), or other suitable electronic data processing components structured to execute instructions provided by the memory. The one or more processors may take the form of a single core processor, a multi-core processor (e.g., dual core, quad core, etc.), micro-processor, etc. In some embodiments, the one or more processors may be external to the apparatus. For example, the one or more processors may be a remote processor (e.g., a cloud-based processor). Alternatively or additionally, the one or more processors may be internal and/or local to the apparatus. In this regard, a circuit or components thereof may be disposed locally (e.g., as part of a local server, a local computing system) or remotely (e.g., as part of a remote server such as a cloud-based server). To that end, a "circuit" as described herein may include components that are distributed across one or more locations. Further, the circuits of the processing circuit described herein may be distributed across one or more locations (e.g., each as part of one or more remote servers).

An example system for implementing the overall system or portions of the embodiments might include a general-purpose computing device in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile storage media may take the form of ROM, flash memory (e.g., flash memory such as NAND, 3D NAND, NOR, 3D NOR), EEPROM, MRAM, magnetic storage, hard disks, optical disks, etc. Combinations of the above are also included within the scope of machine-readable media. In this regard, machine-executable instructions comprise, for example, instructions and data which cause a general-purpose computer, special purpose computer, or special purpose processing machine to perform a certain function or group of functions. Each respective memory device may be operable to maintain or otherwise store data relating to the operations performed by one or more associated circuits, including processor instructions and related data (e.g., database components, object code components, script components), in accordance with the example embodiments described herein.

It should also be noted that the term "input devices," as described herein, may include any type of input device including, but not limited to, a keyboard, a keypad, a mouse, a joystick, or other input devices performing a similar function. Comparatively, the term "output device," as described herein, may include any type of output device including, but not limited to, a computer monitor, printer, facsimile machine, or other output devices performing a similar function.

It should be noted that the term "field," as described herein may include any form of an input field through which the user interfaces shown and described may receive input from a user of a computing device. For instance, the term "field" may include a text field, a drop-down box and selectable options, a lookup box, a search bar, an icon, one or more checkboxes, one or more radio buttons, a button, a toggle, a date field, a slider, and the like. Further, each "field" may include and/or receive data that is associated with a data object as described herein.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principles of the disclosure and its practical application to enable one skilled in the art to utilize the various embodiments and with various modifications as are suited to the particular use contemplated. Other substitutions, modifications, changes, and omissions may be made in the design, operating conditions and embodiment of the embodiments without departing from the scope of the present disclosure as expressed in the appended claim.

What is claimed is:

1. A method for generating an electronic file comprising:
receiving, by a provider computing system, a plurality of first data records from a covered entity computing system;

modifying, by the provider computing system, the plurality of first data records to generate a plurality of modified first data records;

receiving, by the provider computing system, a plurality of second data records from a national health repository;

selecting, by the provider computing system, a first digital projection model and a second digital projection model;

determining, by the provider computing system, a first set of digitally projected records using the first digital projection model based on at least one of: the plurality of modified first data records or the plurality of second data records;

determining, by the provider computing system, a second set of digitally projected records using the second digital projection model based on at least one of: the plurality of modified first data records or the plurality of second data records;

selecting, by the provider computing system, the first set of digitally projected records as a final set of digitally projected records;

storing, by the provider computing system, the selected first set of digitally projected records in a repository;

receiving, by the provider computing system, a request to lock the first digital projection model;

receiving, by the provider computing system, a plurality of new first data records from the covered entity computing system;

modifying, by the provider computing system, the plurality of new first data records to generate a plurality of modified new first data records;

receiving, by the provider computing system, a plurality of new second data records from a national health repository;

determining, by the provider computing system and based on the request to lock the first digital projection model, a third set of digitally projected records using the first digital projection model based on at least one of: the plurality of modified new first data records or the plurality of new second data records;

storing, by the provider computing system, the third set of digitally projected records in the repository;

receiving, by the provider computing system, a file generation request including a file destination address;

generating, by the provider computing system, the electronic file including at least one digitally projected record of the third set of digitally projected records, providing, by the provider computing system, the electronic file to the file destination address of the file generation request.

2. The method of claim 1, wherein the file generation request further includes a query including a configuration property, and wherein the method further includes:
executing, by the provider computing system, the query on the repository to select at least one digitally projected record of the third set of digitally projected records based on the configuration property.

3. The method of claim 2, wherein the configuration property is at least one of: a timeframe, a data record type, a minimum value, and a maximum value.

4. The method of claim 1, wherein the covered entity computing system is a first covered entity computing system associated with a medical claims company, and wherein the plurality of first data records are a plurality of medical claim (Mx) data records, and wherein the method further comprises:

receiving, by the provider computing system, a plurality of prescription claim (Rx) data records from a second covered entity computing system associated with a pharmacy;

modifying, by the provider computing system, the plurality of Rx data records to generate a plurality of modified Rx data records, wherein determining the first set of digitally projected records is based on at least one of: the plurality of modified Mx data records, the plurality of modified Rx data records, or the plurality of second data records, and wherein determining the second set of digitally projected records is based on at least one of: the plurality of modified Mx data records, the plurality of modified Rx data records, or the plurality of second data records.

5. The method of claim 4, wherein the plurality of new first data records are a plurality of new Mx data records, and wherein the method further comprises:

receiving, by the provider computing system, a plurality of new Rx data records from the second covered entity computing system;

modifying, by the provider computing system, the plurality of new Rx data records to generate a plurality of modified new Rx data records, wherein determining the third set of digitally projected records is based on at least one of: the plurality of modified new Mx data records, the plurality of modified new Rx data records, or the plurality of new second data records.

6. The method of claim 1, wherein the first projection model is at least one of: a binary classification model, a neural network model, a multiclass classification model, or a regression model.

7. The method of claim 1, wherein the provider computing system determines the first set of digitally projected values and a first confidence score, wherein the provider computing system determines the second set of digitally projected values and a second confidence score, and wherein the provider computing system selects the first set of digitally projected records as a final set of digitally projected records based on the first confidence score and the second confidence score.

8. A method for generating an electronic file comprising:

receiving, by a provider computing system, a plurality of first data records from a covered entity computing system;

modifying, by the provider computing system, the plurality of first data records to generate a plurality of modified first data records;

selecting, by the provider computing system, a first digital projection model and a second digital projection model;

training, by the provider computing system, the first digital projection model to generate a plurality of first model parameters;

determining, by the provider computing system, a first set of digitally projected records using the first digital projection model based on the plurality of modified first data records and the plurality of first model parameters;

training, by the provider computing system, the second digital projection model to generate a plurality of second model parameters;

determining, by the provider computing system, a second set of digitally projected records using the second digital projection model based on the plurality of modified first data records and the plurality of second model parameters;

selecting, by the provider computing system, the first set of digitally projected records as a final set of digitally projected records;

storing, by the provider computing system, the selected first set of digitally projected records in a first repository;

storing, by the provider computing system, the plurality of first model parameters in a second repository;

receiving, by the provider computing system, a plurality of new first data records from the covered entity computing system;

modifying, by the provider computing system, the plurality of new first data records to generate a plurality of modified new first data records;

selecting, by the provider computing system, the plurality of first model parameters from the second repository;

determining, by the provider computing system, a third set of digitally projected records using the first digital projection model based on the plurality of modified new first data records and the plurality of first model parameters;

storing, by the provider computing system, the third set of digitally projected records in the first repository;

receiving, by the provider computing system, a file generation request including a file destination address;

generating, by the provider computing system, the electronic file including at least one digitally projected record of the third set of digitally projected records;

providing, by the provider computing system, the electronic file to the file destination address of the file generation request.

9. The method of claim 8, wherein the file generation request further includes a query including a configuration property, and wherein the method further includes:

executing, by the provider computing system, the query on the first repository to select at least one digitally projected record of the third set of digitally projected records based on the configuration property.

10. The method of claim 9, wherein the configuration property is at least one of: a timeframe, a data record type, a minimum value, and a maximum value.

11. The method of claim 8, wherein the covered entity computing system is a first covered entity computing system associated with a medical claims company, and wherein the plurality of first data records are a plurality of medical claim (Mx) data records, and wherein the method further comprises:

receiving, by the provider computing system, a plurality of prescription claim (Rx) data records from a second covered entity computing system associated with a pharmacy;

modifying, by the provider computing system, the plurality of Rx data records to generate a plurality of modified Rx data records, wherein determining the first set of digitally projected records is based on the plurality of first model parameters and at least one of: the plurality of modified Rx data records or the plurality of modified Mx data records, and wherein determining the second set of digitally projected records is based on the plurality of second model parameters and at least one of: the plurality of modified Rx data records or the plurality of modified Mx data records.

12. The method of claim 11, wherein the plurality of new first data records are a plurality of new Mx data records, and wherein the method further comprises:

receiving, by the provider computing system, a plurality of new Rx data records from the second covered entity computing system;

modifying, by the provider computing system, the plurality of new Rx data records to generate a plurality of modified new Rx data records, wherein determining the third set of digitally projected records is based on the plurality of first model parameters and at least one of: the plurality of modified new Mx data records or plurality of modified new Rx data records.

13. The method of claim 8, wherein the first projection model is at least one of: a binary classification model, a neural network model, a multiclass classification model, or a regression model.

14. The method of claim 8, wherein the provider computing system determines the first set of digitally projected values and a first confidence score, wherein the provider computing system determines the second set of digitally projected values and a second confidence score, and wherein the provider computing system selects the first set of digitally projected records as a final set of digitally projected records based on the first confidence score and the second confidence score.

15. The method of claim 8, wherein the first set of digitally projected records and the second set of digitally projected records are projected for a first timeframe, and wherein the third set of digitally projected records are projected for a second timeframe, and wherein the second timeframe is shorter than the first timeframe.

16. The method of claim 8, wherein the first timeframe is a month, and wherein the second timeframe is at least one of a: a week or a day.

17. A method for generating an electronic file comprising:

receiving, by a provider computing system, a plurality of first data records from a covered entity computing system;

modifying, by the provider computing system, the plurality of first data records to generate a plurality of modified first data records;

selecting, by the provider computing system, a first digital projection model and a second digital projection model;

determining, by the provider computing system, a first set of digitally projected records using the first digital projection model based on the plurality of modified first data records;

determining, by the provider computing system, a second set of digitally projected records using the second digital projection model based on the plurality of modified first data records;

selecting, by the provider computing system, the first set of digitally projected records as a final set of digitally projected records;

storing, by the provider computing system, the selected first set of digitally projected records in a repository;

receiving, by the provider computing system, a request to lock the first digital projection model;

receiving, by the provider computing system, a plurality of new first data records from the covered entity computing system;

modifying, by the provider computing system, the plurality of new first data records to generate a plurality of modified new first data records;

determining, by the provider computing system and based on the request to lock the first digital projection model, a third set of digitally projected records using the first digital projection model based on at least one of: the plurality of modified new first data records or the plurality of first data records;

storing, by the provider computing system, the third set of digitally projected records in the repository;

receiving, by the provider computing system, a file generation request including a query and a file destination address, wherein the query includes a configuration property;

executing, by the provider computing system, the query on the repository to select at least one digitally projected record of the third set of digitally projected records based on the configuration property;

generating, by the provider computing system, the electronic file including the at least one digitally projected record of the third set of digitally projected records, providing, by the provider computing system, the electronic file to the file destination address of the file generation request.

18. The method of claim 17, wherein the covered entity computing system is a first covered entity computing system associated with a medical claims company, and wherein the plurality of first data records are a plurality of medical claim (Mx) data records, and wherein the method further comprises:

receiving, by the provider computing system, a plurality of prescription claim (Rx) data records from a second covered entity computing system associated with a pharmacy;

modifying, by the provider computing system, the plurality of Rx data records to generate a plurality of modified Rx data records, wherein determining the first set of digitally projected records is based on at least one of: the plurality of modified Mx data records or the plurality of modified Rx data records, and wherein determining the second set of digitally projected records is based on at least one of: the plurality of modified Mx data records or the plurality of modified Rx data records.

19. The method of claim 18, wherein the plurality of new first data records are a plurality of new Mx data records, and wherein the method further comprises:

receiving, by the provider computing system, a plurality of new Rx data records from the second covered entity computing system;

modifying, by the provider computing system, the plurality of new Rx data records to generate a plurality of modified new Rx data records, wherein determining the third set of digitally projected records is based on at least one of: the plurality of modified new Mx data records, the plurality of modified new Rx data records, the plurality of modified Mx data records, or the plurality of modified Rx data records.

20. The method of claim 17, wherein the first projection model is at least one of: a binary classification model, a neural network model, a multiclass classification model, or a regression model.

\* \* \* \* \*